(12) United States Patent
Lee

(10) Patent No.: US 9,682,074 B2
(45) Date of Patent: *Jun. 20, 2017

(54) CRYSTAL FORM

(71) Applicant: Glaxo Group Limited, Brentford, Middlesex (GB)

(72) Inventor: Mei-yin Lee, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,997

(22) Filed: Nov. 25, 2015

(65) Prior Publication Data

US 2016/0075685 A1 Mar. 17, 2016

Related U.S. Application Data

(63) Continuation of application No. 14/241,913, filed as application No. PCT/EP2012/067027 on Aug. 31, 2012, now Pat. No. 9,227,953.

(60) Provisional application No. 61/530,104, filed on Sep. 1, 2011.

(51) Int. Cl.
| | |
|---|---|
| *A61K 31/47* | (2006.01) |
| *A61K 31/4709* | (2006.01) |
| *C07D 401/12* | (2006.01) |

(52) U.S. Cl.
CPC ........ *A61K 31/4709* (2013.01); *C07D 401/12* (2013.01); *C07B 2200/13* (2013.01)

(58) Field of Classification Search
None
See application file for complete search history.

(56) References Cited

U.S. PATENT DOCUMENTS 9,227,953 B2 * 1/2016 Lee ...................... C07D 401/12

FOREIGN PATENT DOCUMENTS

| EP | 2764866 A1 | 8/2014 |
|---|---|---|
| JP | 2004-512283 T | 4/2004 |
| WO | WO 02/30904 A1 | 4/2002 |
| WO | WO2008/140449 A1 | 11/2008 |

OTHER PUBLICATIONS

Acharya, N.K. et al., Diabetes and Hypercholesterolemia Increase Blood-Brain Barrier Permeability and Brain Amyloid Deposition: Beneficial Effects of the LpPLA2 Inhibitor Darapladib; Journal of Alzheimer's Disease 35 (2013) 179-198.
Brittain, H.G. "Polymorphism in Pharmaceutical Solids", 2$^{nd}$ Edition, Informa Healthcare, NY 2009, Table of Contents, Chapters 1 (Brittain), 9 (Bhattacharrya et al.), 10 (Brittain), and 11 (Tishmack))(e.g., pp. 1-4, 15-19, 318-430, e.g. 334-335).
Correa, C.; Working paper—Guidelines for the examination of pharmaceutical patents: developing a public health perspective; Jan. 2007; WHO—ICTSD—NCTAD; cover, i-viii, 1-56.
Kennard, O. et al.; International Union of Crystallography—Commission on Crystallographic Data—Powder Data; J. Appl. Cryst. (1971) 4, 81-86.
Llinas, A. et al.; Polymorph control: past, present and future; Drug Discovery Today; vol. 13; Nos. 5/6; Mar. 2008; 198-210.
GSK—Clinical Study Register (rilapladib/SB-659032)—Study 102487 protocol summary; http://www.gsk-clinicalstudyregister.com/study/102487#ps; 1$^{st}$ received Dec. 6, 2012; A Single Dose Study to Assess the Effect of Non-Bioenhanced, Non-Enteric Coated, Freebase SB-659032 on Platelet Function in Healthy Adult Subjects; Study Start Sep. 2004.
GSK—Clinical Study Register (rilapladib/SB-659032)—Study 104623 protocol summary; http://www.gsk-clinicalstudyregister.com/study/104623#ps; 1$^{st}$ received Dec. 6, 2012; A Double Blind Study to Evaluate Effects of Repeat Doses of SB-659032 on Platelet Aggregation in Healthy Volunteers; Study Start Jul. 2005.
GSK—Clinical Study Register (rilapladib/SB-659032)—Study LP2108364 protocol summary; http://www.gsk-clinicalstudyregister.com/study/LP2108364#ps; 1$^{st}$ received May 31, 2012; A Double Blind, Placebo controlled, Parallel Study to Evaluate Effects of Repeat Doses of Rilapladib on Platelet Aggregation in Healthy Male Volunteers; Study Start Oct. 2006.
ClinicalTrials.gov—ClinicalTrials.gov Identifier: NCT00387257; https://clinicaltrials.gov/ct2/show/NCT00387257?term=rilapladib &rank=3; 1st received: Oct. 10, 2006; Effect Of Rilapladib (SB-659032) On Platelet Aggregation (Study 2108364).
Shaddinger BC, et al., Platelet aggregation unchanged by lipoprotein-associated phospholipase A2 inhibition: results from an in vitro study and two randomized phase I trials. PLoS One. Jan. 27, 2014;9(1):e83094. doi: 10.1371/journal.pone.0083094. eCollection 2014. p. 1-10.
GSK—Clinical Study Register (rilapladib/SB-659032)—Study LP2105521 protocol summary; http://www.gsk-clinicalstudyregister.com/study/LP210552#ps; 1$^{st}$ received Mar. 20, 2009; A multicenter, randomized, 12 week, double-blind, placebo-controlled, parallel-group, Phase IIa study using 18F fluorodeoxglucose (FDG)-PET to measure the effects of rilapladib on macrophage activity in subjects with atherosclerosis; Study Start Nov. 2008.
GSK—Clinical Study Register (rilapladib/SB-659032)—Study LP2105521 result summary; http://www.gsk-clinicalstudyregister.com/study/LP2105521#rs; 1$^{st}$ received Jan. 26, 2012.
ClinicalTrials.gov—ClinicalTrials.gov Identifier: NCT00695305; https://clinicaltrials.gov/ct2/show/NCT00695305?term=rilapladib &rank=2; 1st received: Jun. 9, 2008; An Imaging Study in Patients With Atherosclerosis Taking Rilapladib or Placebo for 12 Weeks (Study LP2105521).
A Tawakol, et al.;.Effect of Treatment for 12 Weeks With Rilapladib, a Lipoprotein-Associated Phospholipase A2 Inhibitor, on Arterial Inflammation as Assessed With 18F-Fluorodeoxyglucose-Positron Emission Tomography Imaging;.J Am Coll Cardiol. 2014;63(1):86-88.

(Continued)

*Primary Examiner* — Heidi Reese
(74) *Attorney, Agent, or Firm* — Loretta J. Sauermelch; Edward R. Gimmi

(57) ABSTRACT

A novel crystalline form of a compound is disclosed.

30 Claims, 8 Drawing Sheets

(56) References Cited

OTHER PUBLICATIONS

GSK—Clinical Study Register (rilapladib/SB-659032)—Study 114458 protocol summary; http://www.gsk-clinicalstudyregister.com/study/114458#ps; 1$^{st}$ received Sep. 1, 2011; A phase 2a study to evaluate the effect of rilapladib (SB-659032) on biomarkers related to the pathogenesis and progression of Alzheimer's disease; Study Start Oct. 2011.
GSK—Clinical Study Register (rilapladib/ SB-659032)—Study 114458 result summary; http://www.gsk-clinicalstudyregister.com/study/114458#rs; 1$^{st}$ received Oct 4, 2013.
ClinicalTrials.gov—ClinicalTrials.gov Identifier:NCT01428453; https://clinicaltrials.gov/ct2/show/NCT01428453?term=rilapladib&rank=4; 1$^{st}$ received: Sep. 1, 2011; A Phase 2a Study to Evaluate the Effect of Rilapladib (SB-659032) in Alzheimer's Disease (Study 114458).
Maher-Edwards, G. et al., A 24-week Study to Evaluate the Effect of Rilapladib on Cognition and CSF Markers of Alzheimer's Disease; Alzheimer's & Dementia: The Journal of the Alzheimer's Association 10, No. 4 (2014) p. 301-302.
Maher-Edwards, G. et al., A 24-week Study to Evaluate the Effect of Rilapladib on Cognition and Cerebrospinal Fluid Biomarkers of Alzheimer's Disease; Alzheimer's & Dementia: Translational Research & Clinical Interventions (2015) 1-10 (Article in Press), and Supplemental Materials (15 pages).
Takashi Kojima et al., "Effective selection of crystal form in pharmaceutical development Application of Raman spectroscopy to salt and polymorphs screening," Pharm Tech Japan, 2007, vol. 23, No. 12, pp. 173(2461)-181(2469) Abstract Only.
Japanese Patent Application No. 2014-527685—Notification of Reason for Rejection, dated Jul. 1, 2016 (Translation of Official Action); pp. 1-5 (particularly pp. 1, 3-4).
Yukinori Takada, "API form screening and selection in drug discovery stage" Pharm Stage, 2007, vol. 6, No. 10, pp. 20-25 (Japanese).
Yukinori Takada, "API form screening and selection in drug discovery stage" Pharm Stage, 2007, vol. 6, No. 10, pp. 20-25 (English language machine translation).
Hiroshi Ohshima, "Crystallization of Polymorphs and Pseudopolymorphs and its Control," Pharm Stage, 2007, vol. 6, No. 10, pp. 48-53 (Japanese).
Hiroshi Ohshima, "Crystallization of Polymorphs and Pseudopolymorphs and its Control," Pharm Stage, 2007, vol. 6, No. 10, pp. 48-53 (English language machine translation).
Takashi Kojima et al, "Effective selection of crystal form in pharmaceutical development Application of Raman spectroscopy to salt and polymorphs screening," Pharm Tech Japan, 2007, vol. 23, No. 12, pp. 173(2461)-181(2469) (Japanese).
Takashi Kojima et al, "Effective selection of crystal form in pharmaceutical development Application of Raman spectroscopy to salt and polymorphs screening," Pharm Tech Japan, 2007, vol. 23, No. 12, pp. 173(2461)-181(2469) (English language abstract 2007:1384837 HCAPLUS).
Takashi Kojima et al, "Effective selection of crystal form in pharmaceutical development Application of Raman spectroscopy to salt and polymorphs screening," Pharm Tech Japan, 2007, vol. 23, No. 12, pp. 173 (2461)-181(2469) (English language machine translation).
Stahly, P., "The Importance of Salt Selection and Polymorph Screening for the Drug Product," Pharmacy, 2006, vol. 66, No. 6, pp. 435-439 (Japanese).
Stahly, P., "The Importance of Salt Selection and Polymorph Screening for the Drug Product," Pharmacy, 2006, vol. 66, No. 6, pp. 435-439 (English language abstract 2007:57713 CAPLUS).
Stahly, P., "The Importance of Salt Selection and Polymorph Screening for the Drug Product," Pharmacy, 2006, vol. 66, No. 6, pp. 435-439 (English language machine translation)..
"Standards and Test Methods for New Drug Product," Notification No. 568 of Pharmaceutical Affairs Bureau, May 1, 2001, pp. 1-46 (Japanese).
International Conference on Harmonisation of Technical Requirements for Registration of Pharmaceuticals for Human Use—ICH Harmonised Tripartite Guideline Specifications: Test Procedures and Acceptance Criteria for New Drug Substances and New Drug Products: Chemical Substances—Q6A—Current Step 4 version, dated Oct. 6, 1999, 35 pp. including Specifications pp. 1-31.
Japanese Patent Application No. 2014-527685—Notification of Reason for Rejection, dated Jul. 1, 2016; pp. 1-5 (English language translation of Official Action).
Japanese Patent Application No. 2014-527685—claims as amended Aug. 31, 2015 (claims 1-16) (English language).
U.S. Appl. No. 15/254,160 "Novel Crystal Form", Mei-yin Lee, filed Sep. 1, 2016, continuation of U.S. Appl. No. 14/951,997 Published U.S. patent application US20160367544, published Dec. 22, 2016.

\* cited by examiner

CRYSTAL FORM

The present invention relates to a novel crystalline form of the Lp-PLA2 inhibitor compound N-[1-(2-methoxyethyl)-piperidin-4-yl]-2-[2-(2,3-difluorobenzylthio)-4-oxo-4H-quinolin-1-yl]-N-(4'-trifluoromethylbiphenyl-4-ylmethyl)acetamide (also referred to herein as rilapladib), pharmaceutical formulations comprising this crystalline form, their use in therapy and processes for preparing the same.

BACKGROUND OF THE INVENTION

The compound rilapladib is described and exemplified, for example, in PCT publication WO02/30904A1, published Apr. 18, 2002 and its worldwide counterparts, the subject matter of which is incorporated herein by reference in their entirety. The compounds disclosed in this application, including rilapladib, are inhibitors of the enzyme Lp-PLA$_2$ and as such are expected to be of use in therapy in disorders mediated by Lp-PLA$_2$ activity such as the disorders disclosed therein. For example, such diseases may be associated with increased involvement of monocytes, macrophages or lymphocytes, with the formation of lysophosphatidylcholine and oxidised free fatty acids, with lipid oxidation in conjunction with Lp-PLA$_2$ activity, or with endothelial dysfunction. Examples of such diseases include atherosclerosis, diabetes, hypertension, angina pectoris, rheumatoid arthritis, stroke, inflammatory conditions of the brain such as Alzheimer's Disease, myocardial infarction, ischaemia, reperfusion injury, sepsis, acute inflammation, chronic inflammation, and psoriasis. Other disorders associated with Lp-PLA$_2$ activity have been described in the art. Rilapladib is currently in a Phase 2 clinical study relating to treatment of Alzheimer's Disease. See, e.g., ClinicalTrials.gov, Study NCT01428453.

Prior to the present invention, two forms of rilapladib had been recognized. A crystalline form of rilapladib had been identified and for the sake of identification had been termed "Form 1". Another form, termed "Form 2" for the sake of identification, was less well defined. Without intending to be bound, Form 2 is thought to be a channel entity which is able to incorporate a range of solvents. While broadly similar and clearly related, solid state characterizations such as XRPD and others may vary for products termed "Form 2" depending on the solvent composition.

WO02/30904A1 Example 5 relating to a preparation of rilapladib does not describe the resulting crystalline form and in particular does not describe the new crystal form according to the present invention. The sample prepared in accordance with Example 5 has been found by XRPD and Raman spectroscopy to comprise Form 1 and Form 2 rilapladib, with no evidence within detection limits of the novel form according to the present invention.

In the course of several experiments, it has now been unexpectedly discovered that rilapladib can be prepared as a new and advantageous crystalline form which for the sake of identification is termed herein as "Form 3".

BRIEF SUMMARY OF THE INVENTION

As one aspect, the present invention provides a crystalline form of rilapladib characterized by an X-ray powder diffraction ("XRPD") pattern substantially in accordance with FIG. 1.

In another aspect, the present invention provides a crystalline form of rilapladib characterized by an XRPD pattern comprising diffraction angles (2 theta) at least at positions of about 6.2, 7.6, 9.1, 11.2, and 14.3 degrees.

As another aspect, the present invention provides a crystalline form of rilapladib characterized by an XRPD pattern comprising diffraction angles (2 theta) at least at positions of about 6.2, 7.6, 9.1, 11.2, 11.7, 12.4, 13.1, 14.0, 14.3, 14.9, 15.3, 16.5, 16.8, 17.5, 17.8, 18.5, 18.9, 19.3, 20.0, 20.6, 21.1, and 22.1 degrees.

As another aspect, the present invention provides a crystalline form of rilapladib characterized by a Raman spectrum substantially in accordance with FIG. 2.

As another aspect, the present invention provides a crystalline form of rilapladib characterized by a Raman spectrum comprising peaks at least at positions of about 103, 276, 752, 1155, 1336, 1623, and 3075 cm-1.

As another aspect, the present invention provides a crystalline form of rilapladib characterized by a Raman spectrum comprising peaks at least at positions of about 3075, 2952, 1623, 1611, 1576, 1528, 1467, 1336, 1288, 1179, 1155, 808, and 103 cm-1.

As a another aspect, the present invention provides a crystalline form of rilapladib characterized by a Raman spectrum comprising peaks at least at positions of about 103, 159, 186, 276, 519, 524, 613, 628, 694, 736, 752, 766, 776, 808, 820, 1038, 1155, 1179, 1288, 1336, 1467, 1528, 1576, 1611, 1623, 2933, 2952, and 3075 cm-1.

In another aspect, the present invention provides a form of crystalline rilapladib characterized by a melting point of from about 165° C. to about 185° C., e.g., from about 170° C. to about 180° C.

In another aspect, the present invention provides a form of crystalline rilapladib characterized by infrared (IR) absorption spectrum (e.g., attenuated total reflectance infrared or "ATR-IR") substantially in accordance with FIG. 7.

As another aspect, the present invention provides a form of crystalline rilapladib characterized by an IR (e.g. ATR-IR) absorption spectrum, comprising peaks at least at about wavenumber 2931, 1652, 1621, 1595, 1528, 1494, 1478, 1423, 1403, 1327, 1317, 1286, 1237, 1204, 1187, 1166, 1140, 1109, 1066, 1024, 992, 969, 932, 865, 859, 813, 795, 767, 751, 708, and 693.

In another aspect, the present invention provides a form of crystalline rilapladib characterized by one or more of (i.e., at least one of) the aforementioned XRPD patterns and one or more of the aforementioned Raman spectra.

In another aspect, the present invention provides a form of crystalline rilapladib characterized by one or more of the aforementioned XRPD patterns, one or more of the aforementioned Raman spectra, and one or more of the aforementioned melting points.

In another aspect, the present invention provides a form of crystalline rilapladib characterized by one or more of the aforementioned XRPD patterns, one or more of the aforementioned Raman spectra, one or more of the aforementioned melting points, and one or more of the aforementioned IR spectra.

In another aspect, the present invention provides a form of crystalline rilapladib characterized by at least two properties, selected from an XRPD pattern, a Raman spectrum, a melting point, and an IR spectrum, wherein those properties are as defined according to any one of the aforementioned embodiments.

As another aspect, the present invention provides a pharmaceutical composition comprising one or more of the above mentioned crystalline forms of rilapladib, referred to herein as Form 3, and one or more pharmaceutically acceptable carriers. In some embodiments, the pharmaceutical composition further comprises another form of rilapladib.

In other aspects, the present invention provides: a method for the treatment of a disease or disorder mediated by Lp-PLA$_2$ in a subject (e.g. a mammal, e.g. a human) comprising administering to the subject an effective amount of rilapladib Form 3; rilapladib Form 3 for use in therapy; and the use of rilapladib Form 3 in the preparation of a medicament for the treatment of a disease or disorder mediated by Lp-PLA$_2$.

As another aspect, the present invention provides a process for preparing rilapladib Form 3.

Other aspects of the invention will be apparent in light of the present disclosure.

DETAILED DESCRIPTION OF THE INVENTION

All published documents cited herein are hereby incorporated herein by reference in their entirety.

The compound N-[1-(2-methoxyethyl)-piperidin-4-yl]-2-[2-(2,3-difluorobenzylthio)-4-oxo-4H quinolin-1-yl]-N-(4'-trifluoromethylbiphenyl-4-ylmethyl)acetamide

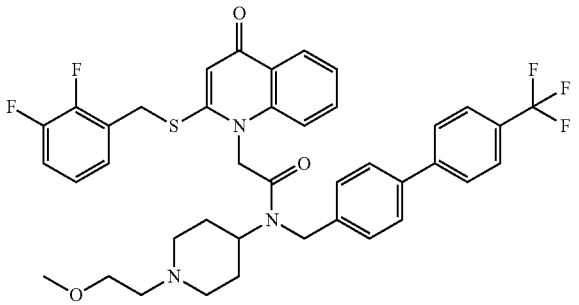 [SMILES: COCCN1CCC(N(Cc2ccc(-c3ccc(C(F)(F)F)cc3)cc2)C(=O)Cn2c(SCc3cccc(F)c3F)cc(=O)c3ccccc32)CC1]

and methods of making and using it are disclosed, for example, in PCT publication WO02/30904. The compound is alternatively known as 2-[2-[(2,3-difluorophenyl)methylsulfanyl]-4-oxoquinolin-1-yl]-N-[1-(2-methoxyethyl)piperidin-4-yl]-N-[[4-[4-(trifluoromethyl)phenyl]phenyl]methyl]acetamide (IUPAC name) and as rilapladib (USAN name).

The present invention provides a novel crystalline form of rilapladib, "Form 3", exhibiting one or more advantageous pharmaceutical properties or other advantages over other forms of rilapladib (e.g., Form 1). For example, rilapladib Form 3 is more thermodynamically stable than Form 1 and Form 2. Therefore, rilapladib Form 3 is more suitable for scale-up and large-scale manufacture associated with pharmaceutical products and reduces the risk of conversion to another form during manufacture, storage or use. In addition to having good stability, rilapladib Form 3 can be obtained in good yield and with reduced energy usage. Rilapladib Form 3 also exhibits very good chemical stability.

Forms of rilapladib, including Form 3 of the present invention, may be characterized and differentiated using a number of conventional analytical techniques, including but not limited to X-ray powder diffraction (XRPD) patterns, Raman spectra, Infrared (IR) absorption spectra, and melting point.

Figure 1:
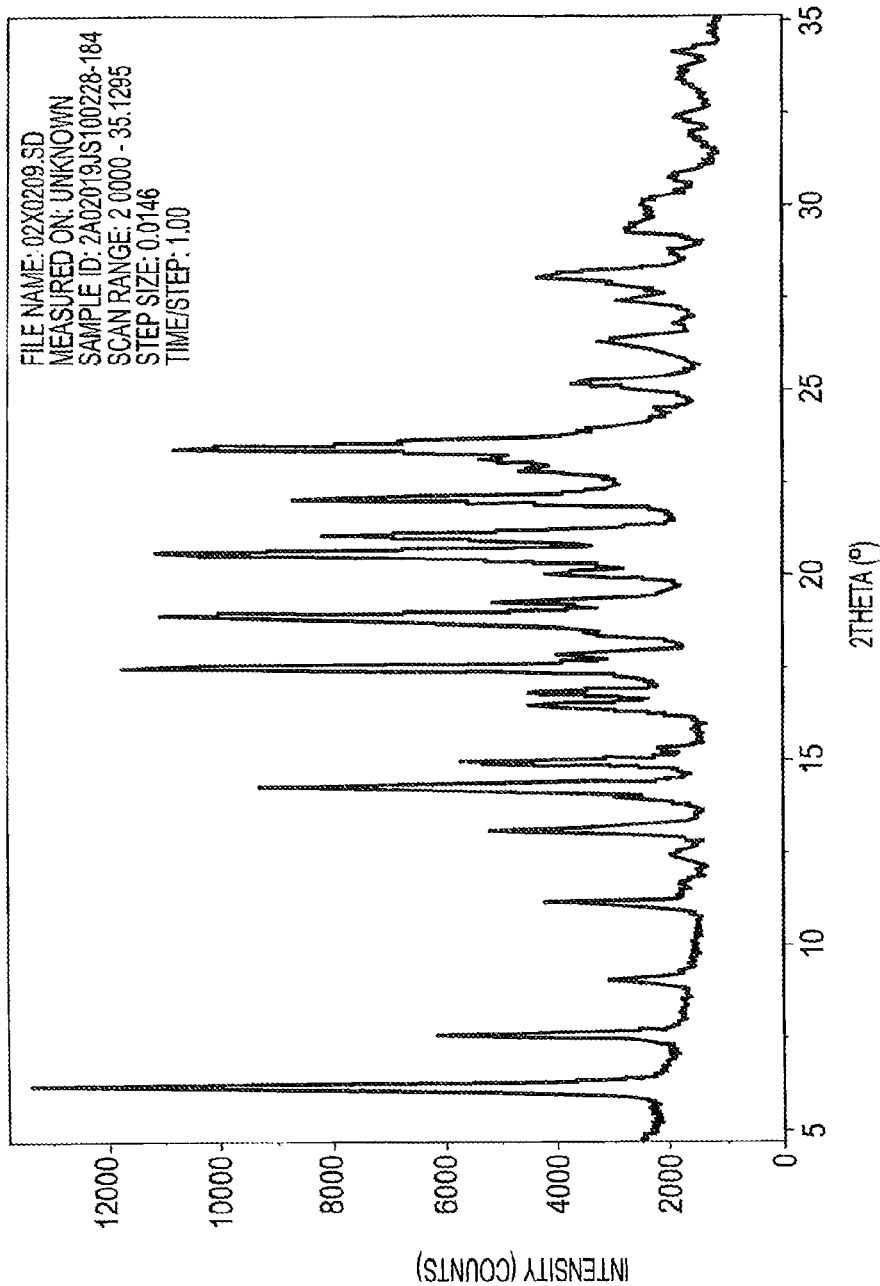
FIG. 1. an example of an XRPD pattern of rilapladib Form 3 according to the present invention.

In one embodiment, the present invention provides a crystalline form of rilapladib characterized by an X-ray powder diffraction ("XRPD") pattern substantially in accordance with FIG. 1.

In another embodiment, the present invention provides a crystalline form of rilapladib characterized by an XRPD pattern comprising diffraction angles (2 theta) at least at positions of about 6.2, 7.6, 9.1, 11.2, and 14.3 degrees (in some embodiments, ±0.1 degrees with respect to each of the foregoing particular peaks).

In another embodiment, the present invention provides a crystalline form of rilapladib characterized by an XRPD pattern comprising diffraction angles (2 theta) at least at positions of about 6.2, 7.6, 9.1, 11.2, 11.7, 12.4, 13.1, 14.0, 14.3, 14.9, 15.3, 16.5, 16.8, 17.5, 17.8, 18.5, 18.9, 19.3, 20.0, 20.6, 21.1, and 22.1 degrees (in some embodiments, ±0.1 degrees with respect to each of the foregoing particular peaks).

Figure 2:
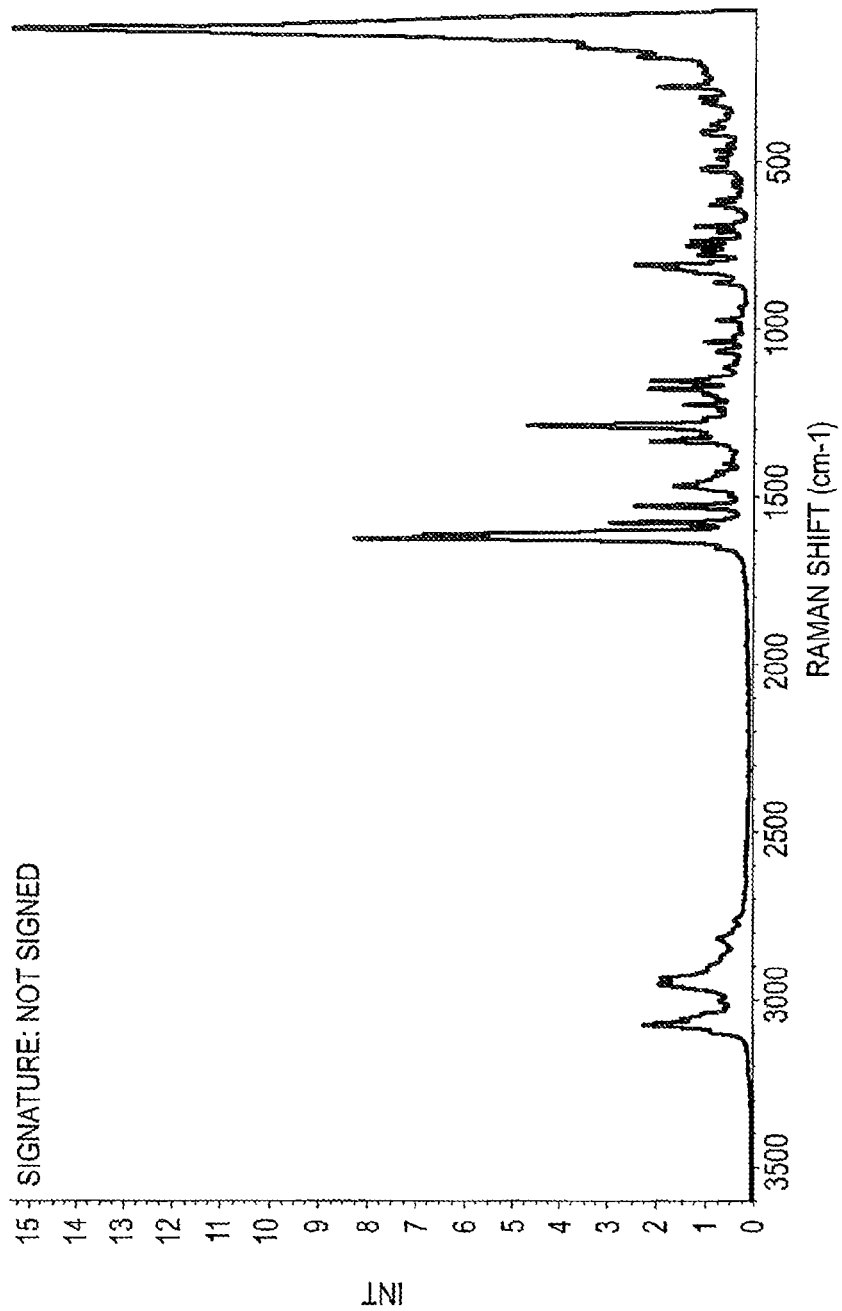
FIG. 2. an example of a Raman spectrum of rilapladib Form 3 according to the present invention.

In another embodiment, the present invention provides a crystalline form of rilapladib characterized by a Raman spectrum substantially in accordance with FIG. 2.

In another embodiment, the present invention provides a crystalline form of rilapladib characterized by a Raman spectrum comprising peaks at least at positions of about 103, 276, 752, 1155, 1336, 1623, and 3075 cm-1 (in some embodiments, ±1 cm$^{-1}$ with respect to each of the foregoing particular peaks).

In another embodiment, the present invention provides a crystalline form of rilapladib characterized by a Raman spectrum comprising significant peaks at least at positions of about 3075, 2952, 1623, 1611, 1576, 1528, 1467, 1336, 1288, 1179, 1155, 808, and 103 cm-1 (in some embodiments, ±1 cm$^{-1}$ with respect to each of the foregoing particular peaks).

In another embodiment, the present invention provides a crystalline form of rilapladib characterized by a Raman spectrum comprising peaks at least at positions of about 103, 159, 186, 276, 519, 524, 613, 628, 694, 736, 752, 766, 776, 808, 820, 1038, 1155, 1179, 1288, 1336, 1467, 1528, 1576, 1611, 1623, 2933, 2952, and 3075 cm-1 (in some embodiments, ±1 cm$^{-1}$ with respect to each of the foregoing particular peaks).

In another embodiment, the present invention provides a form of crystalline rilapladib characterized by one or more of (i.e., at least one of) the aforementioned XRPD patterns and one or more of the aforementioned Raman spectra.

In another embodiment, the present invention provides a form of crystalline rilapladib characterized by a melting point of from about 165° C. to about 185° C., e.g., about 168 to about 182° C., e.g., from about 170° C. to about 180° C.

In some embodiments, the present invention provides a form of crystalline rilapladib characterized by one or more of the aforementioned XRPD patterns, one or more of the aforementioned Raman spectra, and one or more of the aforementioned melting points.

Figure 7:
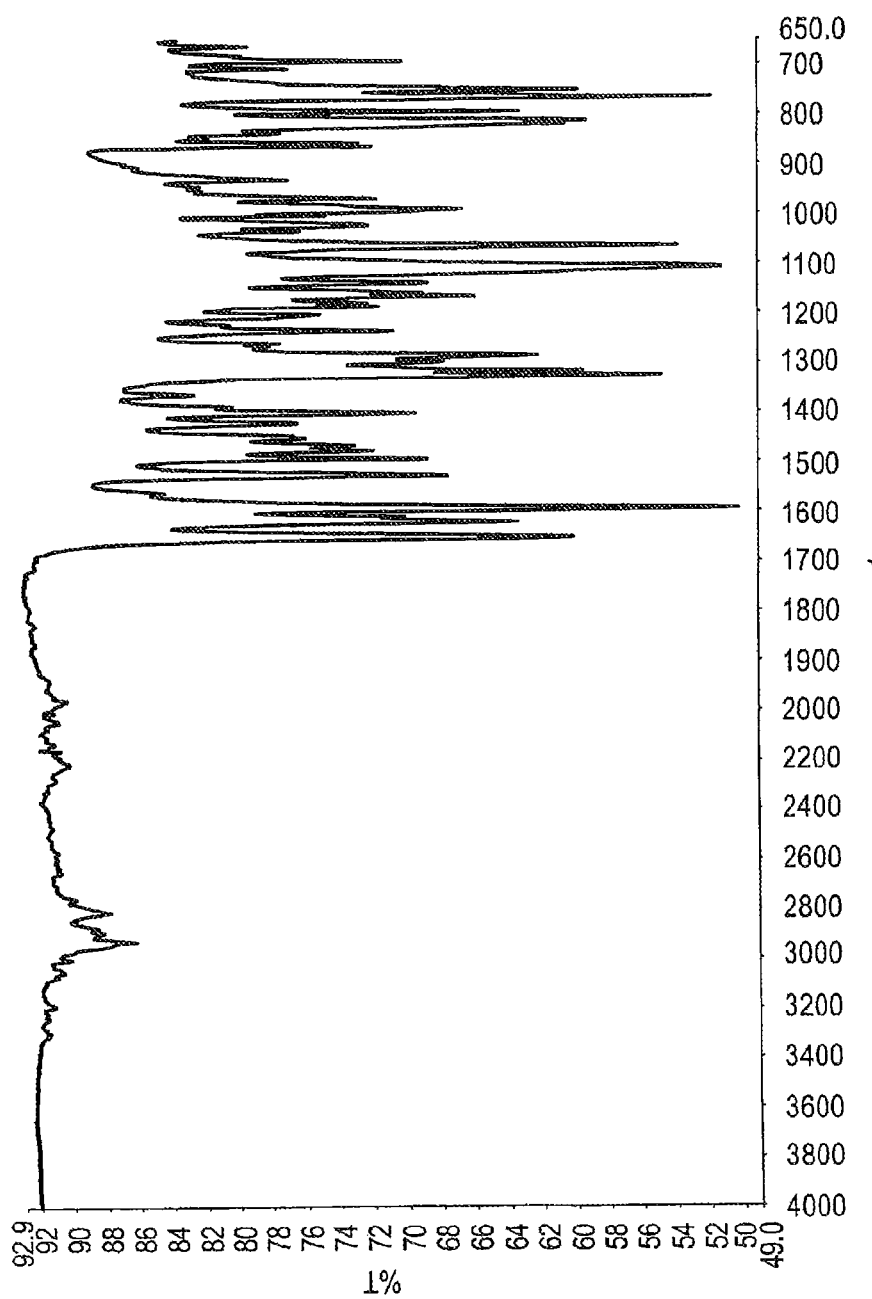
FIG. 7. an example of an ATR-IR absorption spectrum of rilapladib Form 3 according to the present invention.

In another embodiment, the present invention provides a form of crystalline rilapladib characterized by infrared (IR) absorption spectrum (e.g. ATR-IR) substantially in accordance with FIG. 7.

As another embodiment, the present invention provides a form of crystalline rilapladib characterized by an IR (e.g. ATR-IR) absorption spectrum, comprising significant peaks at least at about wavenumber 2931, 1652, 1621, 1595, 1528, 1494, 1478 1423, 1403, 1327, 1317, 1286, 1237, 1204, 1187, 1166, 1140, 1109, 1066, 1024, 992, 969, 932, 865, 859, 813, 795, 767, 751, 708, and 693 (in some embodiments, +/−1 wavenumber with respect to each of the foregoing particular wavenumbers).

In some embodiments, the present invention provides a form of crystalline rilapladib characterized by one or more of the aforementioned XRPD patterns, one or more of the aforementioned Raman spectra, one or more of the aforementioned melting points, and one or more of the aforementioned IR absorption spectra.

As used herein, "Form 3 rilapladib" or "rilapladib Form 3" refers to crystalline rilapladib characterized by at least one of the aforementioned XRPD patterns and/or at least one of the aforementioned Raman spectra and/or at least one of the aforementioned melting points and/or at least one of the aforementioned Infrared spectra.

In some embodiments, the Form 3 rilapladib is characterized by at least two properties selected from an XRPD pattern, a Raman spectrum, a melting point, and an IR absorption spectrum, wherein those properties are as defined according to any one of the aforementioned embodiments.

The X-ray powder diffraction pattern of forms of rilapladib, including Form 3, can be determined using conventional techniques and equipment known to those skilled in the art of analytical chemistry and physical characterization. In some embodiments, such as used for generating FIGS. 1, 3 and 5, the XRPD pattern is obtained with a diffractometer equipped with a diffracted beam graphite monochromator using copper Kα X-radiation.

Figure 3:
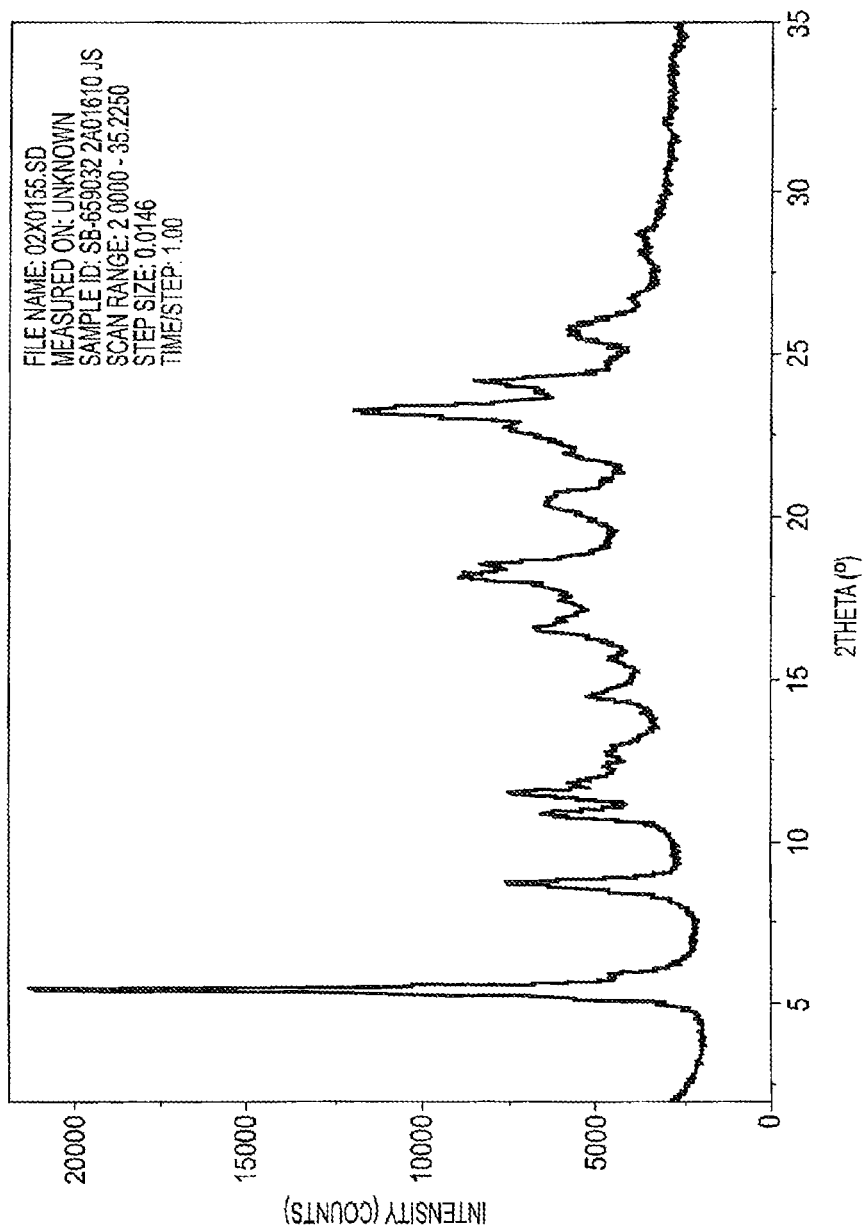
FIG. 3. Comparative—an example of an XRPD pattern of rilapladib Form 1.
Figure 5:
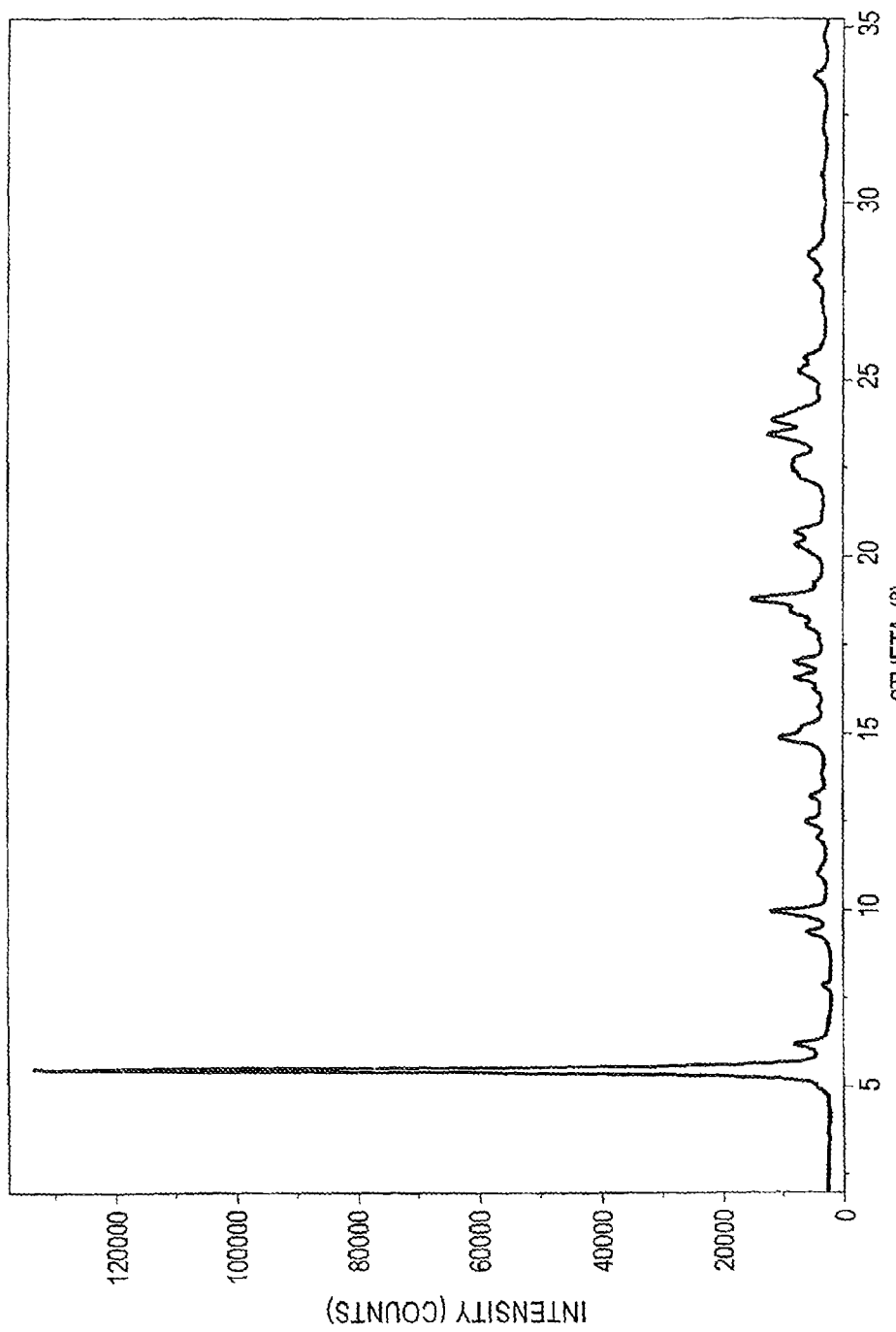
FIG. 5. Comparative—an example of an XRPD pattern of rilapladib Form 2.

The diffraction patterns of FIGS. 1, 3 and 5 were obtained with a Bruker D8 Advance X-Ray powder diffractometer configured with a Cu anode (40 kV, 40 mA), variable divergence slit, primary and secondary Soller slits, and a position sensitive detector. Data were acquired over the range 2-35 degrees 2-theta using a step size of 0.0145 degrees 2-theta (time per step: 1 s). Samples (lightly ground) were packed into top-filled cups that were rotated during data acquisition. In FIGS. 1, 3 and 5, 2-Theta angles in degrees (x-axis) is plotted against peak intensity in terms of the count rate per seconds (y-axis).

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An XRPD pattern that is "substantially in accordance" with that of a Figure provided herein (e.g., FIG. 1) is an XRPD pattern that would be considered by one skilled in the art to represent a compound possessing the same crystal form as the compound that provided the XRPD pattern of that Figure (e.g., FIG. 1). That is, the XRPD pattern may be identical to that of the Figure (e.g., FIG. 1), or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of rilapladib with FIG. 1 and, using expertise and knowledge in the art, readily determine whether the XRPD pattern of the sample is substantially in accordance with the XRPD pattern of FIG. 1 and rilapladib Form 3. If the XRPD pattern is substantially in accordance with FIG. 1, the sample form can be readily and accurately identified as having the same form as rilapladib Form 3. Similarly, a person skilled in the art is capable of determining if a given diffraction angle (expressed in °2θ) obtained from an XRPD pattern is at about the same position as a value presented herein. The same technique may be employed using FIGS. 3 and 5 to determine whether a particular sample is rilapladib Form 1 or rilapladib Form 2 respectively.

One skilled in the art can readily determine the lattice spacings for an XRPD pattern from the diffraction angles and the source of radiation by derivation methods known in the art.

The Raman spectrum of forms of rilapladib, including rilapladib Form 3, can be determined using conventional equipment and techniques known to those skilled in the art of analytical chemistry and physical characterization. In some embodiments, such as used for generating FIGS. 2, 4 and 6, the spectrum is obtained using a FT-Raman spectrometer at 4 cm$^{-1}$ resolution.

Figure 4:
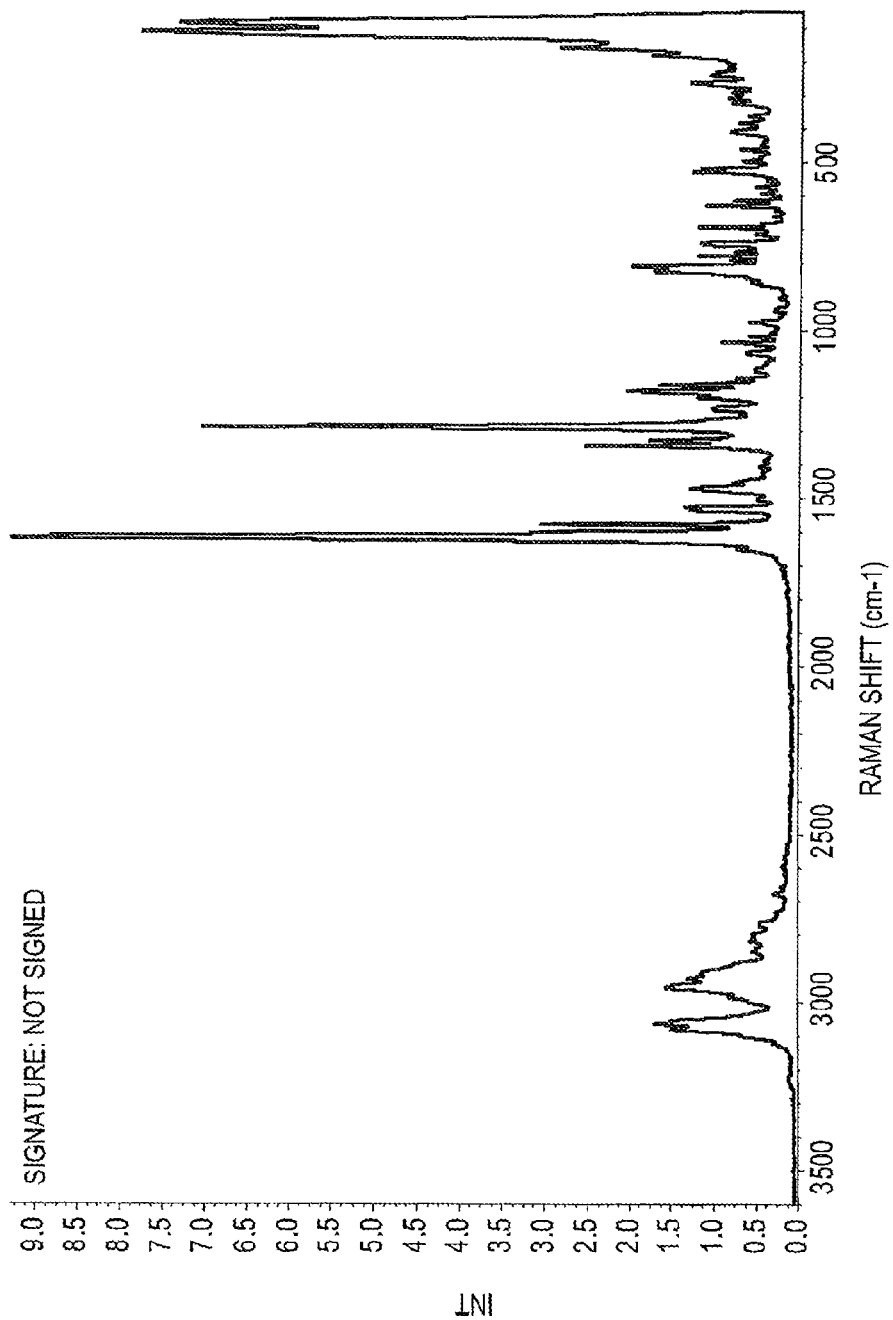
FIG. 4. Comparative—an example of a Raman spectrum of rilapladib Form 1.
Figure 6:
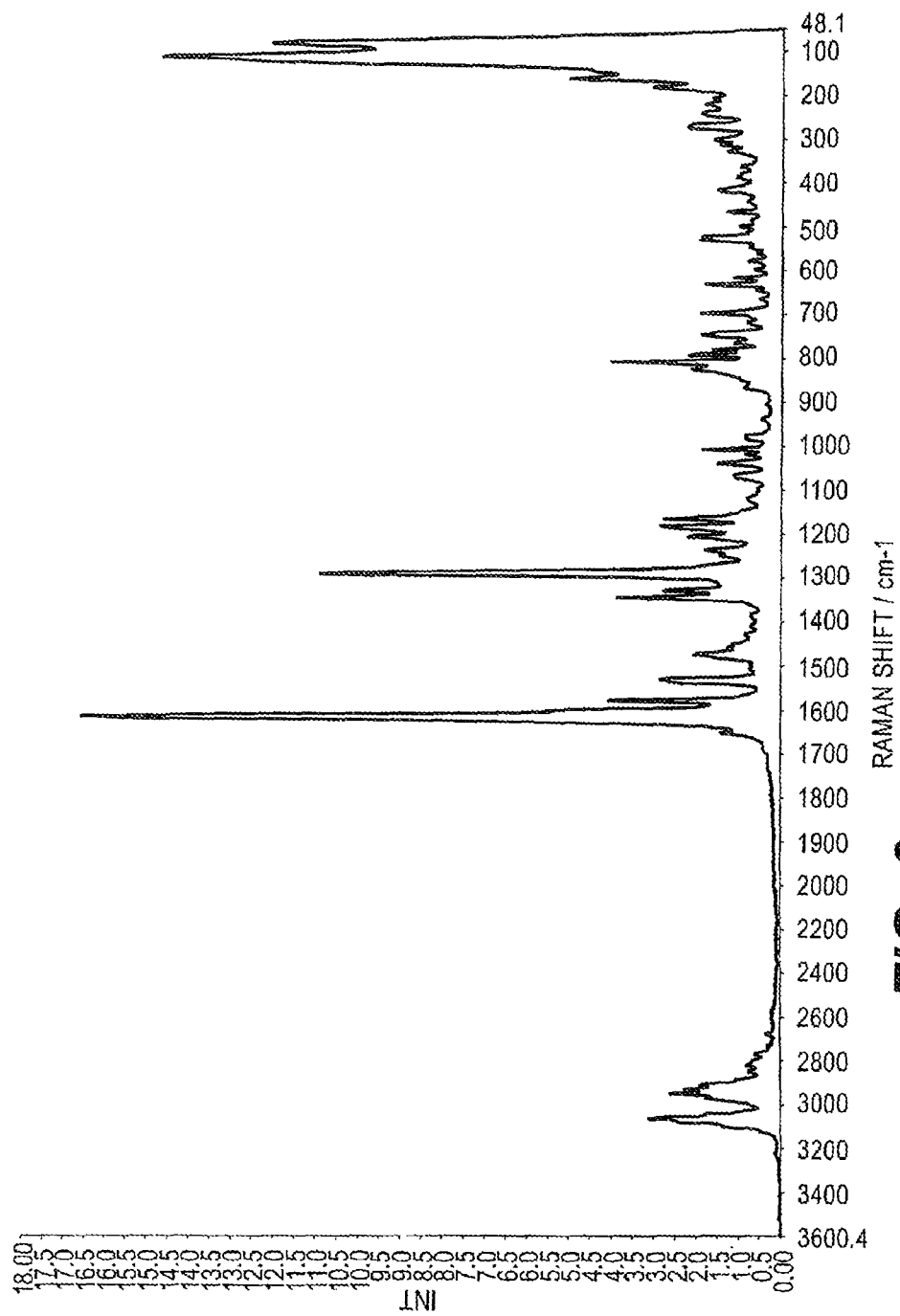
FIG. 6. Comparative—an example of a Raman spectrum of rilapladib Form 2.

The Raman spectra of FIGS. 2, 4 and 6 were obtained using a Nicolet 960 E.S.P. FT-Raman spectrometer. Data were acquired at 4 cm-1 resolution. Laser excitation was at 1064 nm (as is inherent by the use of an FT-Raman spectrometer) with a power of 400 mW. The number of sample scans was 600, using an InGaAs detector and a CaF2 beamsplitter. Sample was prepared by placing the solid sample as received into a glass NMR tube. The sample was rotated during the measurement. Raman shift in cm$^{-1}$ (x-axis) is plotted against Raman intensity (y-axis).

The power (mW) and minimum number of scans accumulation may be adjusted within conventional knowledge to provide a spectrum of similar quality to that provided in FIG. 2, 4 or 6. For example, if a higher power is employed, a lower number of minimum scans accumulation may be required to achieve a spectrum of similar quality to that reported in the Figures. Similarly, if a lower power is employed, a higher number of minimum scans accumulation may be required to obtain a spectrum of similar quality. In some embodiments, the spectrum will be obtained using a power of 400 mW and a minimum of 600 scans accumulation (e.g., 1200 scans).

The choice of detector is not believed to be critical to obtaining a spectrum suitable for comparison with that provided in FIG. 2, 4 or 6. As is known to those skilled in the art, a different detector will likely affect the intensity of the peaks. However, peak positions should remain relatively the same. In some embodiments, the spectrum will be obtained using an InGaAs detector.

Slight variations in observed peaks are expected based upon the specific spectrometer employed and acquisition parameters used. However, this variation should be no more than ±1 wavenumber.

A Raman spectrum that is "substantially in accordance" with that of a Figure provided herein (e.g., FIG. 2) is a Raman spectrum that would be considered by one skilled in the art to represent a compound possessing the same crystal form as the compound that provided the Raman spectrum of that Figure (e.g., FIG. 2). That is, the Raman spectrum may be identical to that of the Figure (e.g., FIG. 2), or more likely it may be somewhat different. Such a Raman spectrum may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of rilapladib with FIG. 2 and, using expertise and knowledge in the art, readily determine whether the Raman spectrum of the sample is substantially in accordance with the Raman spectrum of FIG. 2 and rilapladib Form 3. If the Raman spectrum is substantially in accordance with FIG. 2, the sample form can be readily and accurately identified as having the same form as rilapladib Form 3. Similarly, a person skilled in the art is capable of determining if a given peak obtained from a Raman spectrum is at about the same position as a value presented herein.

Since some margin of error is possible in the marking of peak positions, the preferred method of determining whether an unknown form of rilapladib is rilapladib Form 3 is to overlay the Raman spectrum of the sample with the Raman spectrum of FIG. 2. One skilled in the art can overlay a Raman spectrum of an unknown sample of rilapladib, obtained using the methods described herein, over FIG. 2 and, using expertise and knowledge in the art, readily determine whether the Raman spectrum of the unknown sample is substantially in accordance with FIG. 2 and therefore of the same form as rilapladib Form 3. The same technique may be employed using FIGS. 4 and 6 to determine whether a particular sample is rilapladib Form 1 or rilapladib Form 2 respectively.

Melting points are determined by conventional methods such as capillary tube and may exhibit a range over which complete melting occurs, or in the case of a single number, a melt point of that temperature, +/−1 degree.

It has been found that the melting point of rilapladib Form 3 is significantly higher than that of rilapladib Form 1. In some embodiments, Form 3 rilapladib is characterized by a capillary melting point in the range of from about 165° C. to about 185° C., e.g., about 168° C. to about 182° C., e.g., from about 170° C. to about 180° C., e.g. about 175° C. A melting point in this range is indicative of the presence of Form 3. In contrast, Form 1 provides a capillary tube melting point in the range of about 110° C. to about 125° C. depending on the sample purity (particularly in the range of about 110° C. to about120° C., e.g. about 116° C. to about118° C.). Form 2 tends to provide a similar (capillary tube) melting point range of about 110° C. to about 125° C.

DSC (differential scanning calorimetry) methods such as are known in the art may also be used to determine a phase or form change (e.g. melting) upon controlled heating. Some examples herein report the temperature(s) of the onset of endothermic activity by DSC. For example, depending e.g., on sample purity, Form 3 may have a DSC onset melt in the range of about 170° C. to about 175° C. In contrast, Forms 1 and 2 tend to have at least one DSC endotherm onset which is significantly lower than Form 3 (e.g., in the range of about 100 to about 120° C.).

Those skilled in the art will appreciate that depending on the composition of a particular sample, a material may exhibit a different melt point or endotherm onset, for instance a higher melt point/onset or multiple melt points/onsets including a higher melt point/onset. One or more other solid state characterization methods, such as those disclosed herein, may be used to determine the form(s) present.

The IR spectrum of forms of rilapladib, e.g., rilapladib Form 3, can be determined using conventional equipment and techniques known to those skilled in the art of analytical chemistry and physical characterization. The IR spectra of FIGS. 7 and 8 were obtained by attenuated total reflectance (ATR) infrared spectroscopy in accordance with USP, General Chapter <197>, Ph.Eur. 2.2.23, and JP General Test 2.25 recording the spectrum from approximately 4000 cm-1 to 650 cm-1. The wavenumber in $cm^{-1}$ (x-axis) is plotted against percent transmittance (y-axis).

Figure 8:
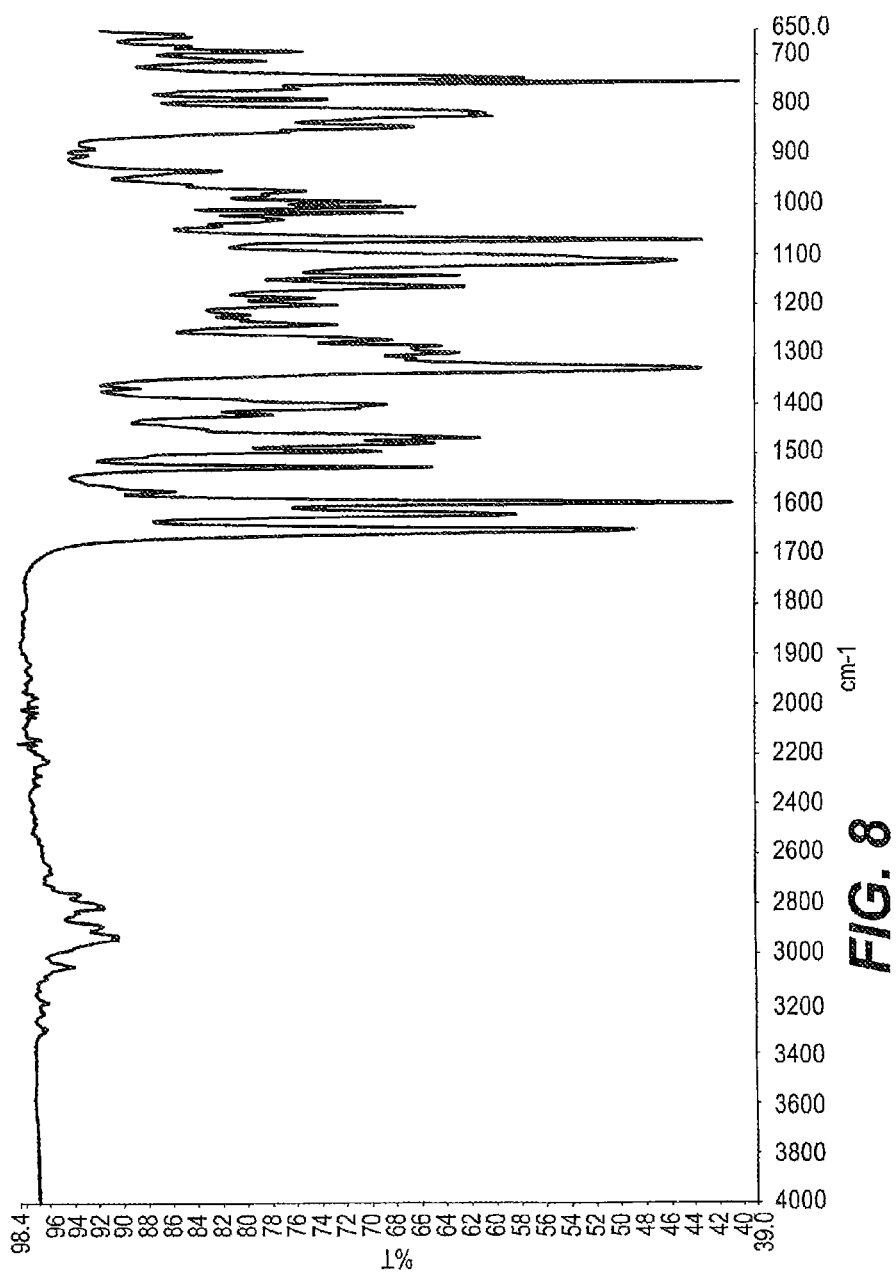
FIG. 8. Comparative—an example of an ATR-IR absorption spectrum of rilapladib Form 1.

More specifically, the IR spectra of FIGS. 7 and 8 were obtained using a PerkinElmer Spectrum One equipped with the PerkinElmer Universal Attenuated Total Reflectance (ATR) pod fitted with the Diamond/Zinc Selenide composite single bounce ATR (DATR) crystal. The data were acquired at 2 cm-1 resolution and 16 scans were acquired. The sample was prepared by crushing it as received using the ATR accessory.

Slight variations in observed IR peaks are expected based upon the specific spectrometer employed and acquisition parameters used. However, this variation should be no more than ±1 wavenumber.

An IR spectrum that is "substantially in accordance" with that of a Figure provided herein (e.g., FIG. 7) is an IR spectrum that would be considered by one skilled in the art to represent a compound possessing the same crystal form as the compound that provided the IR spectrum of that Figure (e.g., FIG. 7). That is, the IR spectrum may be identical to that of the Figure (e.g., FIG. 7), or more likely it may be somewhat different. A person skilled in the art is capable of determining if a sample of a crystalline compound has the same form as, or a different form from, a form disclosed herein by comparison of their IR spectra. For example, one skilled in the art can overlay an IR spectrum of a sample of rilapladib with FIG. 7 and, using expertise and knowledge in the art, readily determine whether the IR spectrum of the sample is substantially in accordance with the IR spectrum of FIG. 7 and rilapladib Form 3. If the IR spectrum is substantially in accordance with FIG. 7, the sample form can be readily and accurately identified as having the same form as rilapladib Form 3. Similarly, a person skilled in the art is capable of determining if a given peak obtained from a IR spectrum is at about the same position as a value presented herein. The same technique may be employed using FIG. 8 to determine whether a particular sample is rilapladib Form 1.

Since some margin of error is possible in the marking of peak positions, the preferred method of determining whether an unknown form of rilapladib is rilapladib Form 3 is to overlay the IR spectrum of the sample with the IR spectrum of FIG. 7. One skilled in the art can overlay an IR spectrum of an unknown sample of rilapladib, obtained using the methods described herein, over FIG. 7 and, using expertise and knowledge in the art, readily determine whether the IR spectrum of the unknown sample is substantially in accordance with FIG. 7 and therefore of the same form as rilapladib Form 3. The same technique may be employed using FIG. 8 to determine whether a particular sample is rilapladib Form 1.

In some embodiments, the rilapladib Form 3 has a water of hydration content of not more than 3% by weight (w/w), in more particular embodiments not more than 2% w/w, 1.5% w/w, 1% w/w, 0.7% w/w, or not more than 0.5% w/w. As used herein, "anhydrous" refers to a water of hydration content of ≤5% w/w. The water of hydration content may be measured by the Karl Fischer method which is well known in the art and is described, for example, in the 1990 US Pharmacopoeia at pages 1619-1621, and the European Pharmacopoeia, second edition (1992) part 2, sixteenth fascicule at v. 3.5-6.1.

In some embodiments, Form 3 is nonhygroscopic.

In some embodiments, the rilapladib Form 3 is substantially pure. As used herein, the term "substantially pure", when used in reference to a solid state form (such as a polymorph or polyamorph) of rilapladib, refers to the solid state form (e.g. Form 3) which is at least 90% by weight pure. This means that the form of rilapladib contains less than 10% by weight of any other compound and, in particular, contains less than 10% by weight of any other form of rilapladib. In particular embodiments, substantially pure refers to a solid state form which is at least 95% pure, at least 97% pure, or at least 99% pure by weight. This means that the form of rilapladib contains less than 5%, 3%, or 1% by weight respectively of any other compound and, in particular, contains less than 5%, 3%, or 1% by weight respectively of any other form of rilapladib. Substantial purity can be determined using conventional methods such as are known in the art, e.g. High Performance Liquid Chromatography (HPLC) and methods such as disclosed herein for identifying forms in a mixture of crystal forms.

In some embodiments, the rilapladib Form 3 comprises 1% by weight solvent(s). Percent solvent can be readily determined using conventional methods such as are known in the art, e.g. Gas Chromatography. Thermogravimetric analysis by methods such as known in the art may also be used to determine the solvent or water content of a material, by providing percent weight loss on heating.

In some embodiments, the rilapladib Form 3 is characterized by the following properties: an IR spectrum substantially in accordance with FIG. 7; a substantial purity of ≥97 weight % (by HPLC on water and solvent free basis); a total solvent content of ≤1 weight %; and a water of hydration content of ≤0.5 weight %. In particular embodiments, such rilapladib Form 3 is further characterized by having an XRPD pattern substantially in accordance with FIG. 1 and/or a melting point of about 175° C. (e.g. by Differential Scanning calorimetry or "DSC").

The present invention includes Form 3 rilapladib both in substantially pure form and in admixture with one or more other forms of rilapladib (including, e.g., a mixture comprising more than 10 weight % total of one or more other forms). Other forms of rilapladib include one or more other polymorphs, including but not limited to Form 1, and/or one or more solvates including but not limited to hydrates. As will be recognized by those skilled in the art, polymorphs may be essentially anhydrous or be solvated (e.g., hydrated).

Admixtures of Form 3 rilapladib with another form(s) of rilapladib may result in the masking or absence of one or more of the foregoing X-ray powder diffraction peaks, Raman spectrum peaks, and IR peaks disclosed herein for Form 3 rilapladib. Methods are known in the art for analyzing such admixtures of forms in order to provide for the accurate identification of the presence or absence of a particular form in the admixture. Suitable methods for the identification and/or quantitation of the particular forms in a mixture are well known in the art, e.g., IR, Raman, SSNMR, Near IR (NIR), XRPD and ATR-IR. Admixtures may also result in multiple melt points; presence of a melt point ≥165° C. is indicative of the presence of Form 3.

Processes for preparing rilapladib Form 3 of the invention are also within the ambit of this invention.

In some embodiments, a process for preparing rilapladib Form 3 comprises:
(a) forming a mixture of rilapladib in a solvent,
(b) crystallizing rilapladib from the mixture, where the crystallized material comprises Form 3 rilapladib, and
(c) isolating the crystallized rilapladib comprising Form 3 rilapladib.

In some embodiments, the process further comprises seeding the mixture of rilapladib and solvent with rilapladib Form 3.

In some embodiments, the process further comprises the step of drying the isolated rilapladib comprising Form 3 rilapladib.

In step (a), forming a mixture of rilapladib and solvent, in some embodiments the rilapladib is a form other than Form 3, e.g., Form 1 rilapladib. In some embodiments, the rilapladib is Form 3 (for example, in a recrystallization of Form 3 previously prepared, including from another form such as Form 1).

Suitable solvents include acetonitrile, THF (tetrahydrofuran), ethyl acetate, toluene, heptane, acetone, aqueous ethanol, MIBK, DiMAC, and mixtures thereof. In some particular embodiments, the solvent is or comprises MIBK or a mixture of MIBK and DiMAC.

In some embodiments, the solvent is 1,4-dioxane, 1-butanol, 1-propanol, acetone, acetone:water (1%), acetone:water (50%), cyclohexane, cyclohexanone, DEGDME (diethylene glycol), dimethylether, dimethyl carbonate, dioxane:water (1%), DMA (dimethyl acetamide), DMSO, EtOAc (ethyl acetate), EtOAc:cyclohexane (1:2), EtOAc:toluene (1:2), heptane, IPA (isopropyl alcohol), IPA:iPrOAc (1:2), IPA:water (1%), isopropyl ether (IPE), isopropyl acetate (iPrOAc), MeCN (acetonitrile), MeCN:water (1%), MEK (methyl ethyl ketone), MeOAc (methyl acetate), MeOH (methanol), MeOH:water (1%), MeOH:water (20%), MeOH:water (50%), MIBK, MIBK saturated with water, MIBK:DMA (8:1), NMP (methyl pyrrolidone), PEG(polyethylene glycol) 400, TBME (t-butyl methyl ether), THF:Water (1%), toluene, water or a combination thereof.

In some embodiments, the rilapladib is dissolved in the solvent. In other embodiments, the rilapladib/solvent mixture is a slurry.

The solvent and/or mixture may be heated, e.g., to facilitate dissolution. In some embodiments, the solvent and/or mixture are at ambient temperature, e.g., about 25° C. In other embodiments, the solvent and/or mixture are cooled, e.g., to facilitate crystallization, e.g. to a temperature below ambient.

Step (b) of crystallizing rilapladib from the mixture may optionally comprise cooling the mixture, e.g., cooling from above ambient temperature, or cooling from ambient temperature.

The process may involve heating and/or cooling, or temperature cycling of the solvent and/or mixture such as known in the art of crystallization and recrystallization. In various embodiments, Form 3 is recrystallized from one or more of the above mentioned solvents by preparing a slurry of rilapladib Form 3 in the solvent and temperature cycling, e.g., from about 0° C. to about 40° C. or 50° C., e.g., for about 2-3 days (for instance 48-60 hours).

In some embodiments, the crystallization step is carried out over a period of at least about 12 hours, particularly e.g., at least about 15, 24, 48, 60, or 72 hours (including about 12, 15, 24, 48, 60 and 72 hours).

Step (c) of isolating the crystallized rilapladib may be accomplished by conventional methods such as filtration.

Drying of the isolated material may be accomplished by conventional methods, such as vacuum drying with our without heat.

The present invention encompasses combinations of the aforementioned process embodiments.

Rilapladib is an inhibitor of the enzyme lipoprotein associated phospholipase $A_2$ (Lp-PLA$_2$) and as such is expected to be of use in therapy. Therefore, in one aspect the present invention provides a method of inhibiting Lp-PLA$_2$ in a subject in need thereof, comprising administering to the subject an effective amount of rilapladib Form 3. Therefore, in a further aspect the present invention provides rilapladib Form 3 for use in therapy. Diseases or disorders for which rilapladib Form 3 may be used include those disclosed in WO02/30904A1, WO08/140449, WO2008/141176, WO2012/080497, WO2012/037782, WO2012/075917, WO2012/076435 or in US Patent Application Publication Nos. US 2008/0279846 (published Nov. 13, 2008), US2010/0239565 (published Sep. 23, 2010), or US2008/0280829 (published Nov. 13, 2008), all incorporated herein by reference in their entirety. In some embodiments, rilapladib Form 3 is used for treating a disease or disorder selected from atherosclerosis, diabetes, hypertension, angina pectoris, rheumatoid arthritis, stroke, inflammatory conditions of the brain such as Alzheimer's Disease, myocardial infarction, ischaemia, reperfusion injury, sepsis, acute inflammation, chronic inflammation, psoriasis, diabetic retinopathy, diabetic macular edema, vascular dementia, multiple sclerosis, and skin ulcers.

The invention accordingly includes a method for treating a disorder or disease which is mediated by Lp-PLA$_2$ in a subject in need thereof comprising administering to a subject in need thereof an effective amount of rilapladib Form 3 or a composition thereof.

In some embodiments, the disorder or disease which is mediated by Lp-PLA$_2$ is selected from atherosclerosis, diabetes, hypertension, angina pectoris, rheumatoid arthritis, stroke, inflammatory conditions of the brain such as Alzheimer's Disease, myocardial infarction, ischaemia, reperfusion injury, sepsis, acute inflammation, chronic inflammation, psoriasis, diabetic retinopathy, diabetic macular edema, vascular dementia, multiple sclerosis, and skin ulcers. In particular embodiments, the disorder or disease is Alzheimer's Disease.

In some embodiments of the administration methods herein, the subject is a mammal, e.g. a human.

Administration methods include administering an effective amount of rilapladib Form 3 (including as a pharmaceutical composition comprising rilapladib Form 3) at different times during the course of therapy. The rilapladib Form 3 may be administered in a combination therapy with one or more other pharmaceutical active agents as separate administration of the pharmaceutical active agents and/or administration with at least one other pharmaceutical active agent as a combination dosage form. The methods of the invention include all known therapeutic treatment regimens.

As used herein, "treatment", "treating" and the like includes prophylaxis and refers to ameliorating or alleviating the specified condition, eliminating or reducing one or more symptoms of the condition, slowing or eliminating the onset or progression of the condition, and preventing or delaying the reoccurrence of the condition in a previously afflicted or diagnosed subject. Prophylaxis (prevention or delay of condition onset) is typically accomplished by administering a drug in the same or similar manner as one would to a subject with the developed disease or condition.

"Effective amount" means that amount of drug substance (i.e. rilapladib Form 3, optionally in combination with other pharmaceutical agents including other forms of rilapladib) that elicits the desired biological or medical response in a subject that is being sought, for instance, by a researcher or clinician. Such response includes alleviation of the symptoms of the condition being treated, ameliorating or alleviating the specified condition, eliminating or reducing one or more symptoms of the condition, slowing or eliminating the onset or progression of the condition, preventing or delaying the reoccurrence of the condition in a previously afflicted or diagnosed subject, and/or preventing or delaying onset of the condition being treated.

An embodiment of the invention includes administering rilapladib Form 3 or a pharmaceutical composition containing the same in a combination therapy.

An embodiment of the invention includes administering rilapladib Form 3 or a pharmaceutical composition containing the same in a combination therapy with one or more additional pharmaceutical agents for the treatment of the above-mentioned diseases or disorders. Such additional agents include any of the agents described herein.

Some embodiments of the invention include administering rilapladib Form 3 or a pharmaceutical composition containing the same in a combination therapy with one or more additional agents selected from an anti-hyperlipidaemic, anti-atherosclerotic, anti-diabetic, anti-anginal, anti-inflammatory, or anti-hypertension agent or an agent for lowering Lp(a). Examples of the foregoing include cholesterol synthesis inhibitors such as statins, anti-oxidants such as probucol, insulin sensitisers, calcium channel antagonists, anti-inflammatory drugs such as NSAIDs, and Lp-PLA$_2$ inhibitors. Examples of agents for lowering Lp(a) include the aminophosphonates described in WO 97/02037, WO 98/28310, WO 98/28311 and WO 98/28312 (Symphar SA and SmithKline Beecham). Statins include atorvastatin, simvastatin, pravastatin, cerivastatin, fluvastatin, lovastatin and rosuvastatin. Examples of anti-diabetic agents and insulin sensitizers PPARgamma activators, e.g., GI262570 (GlaxoSmithKline), and the glitazone class of compounds such as rosiglitazone (AVANDIA, GlaxoSmithKline), troglitazone and pioglitazone. Examples of Lp-PLA$_2$ inhibitors include those disclosed in the above-mentioned WO02/30904, WO08/140449, WO2008/141176, WO2012/080497, WO2012/037782, WO2012/075917, WO2012/076435, US 2008/0279846, US2010/0239565 and US2008/0280829; other additional agents that may be used in combination therapy with rilapladib Form 3 are any of the agents disclosed in any of these publications for combined use with the Lp-PLA$_2$ inhibitor.

Some embodiments of the invention include administering rilapladib Form 3 or a pharmaceutical composition containing the same in a combination therapy with one or more additional agents for the treatment of Alzheimer's disease including agents selected from acetylcholinesterase inhibitors, NMDA receptor antagonists, and combinations thereof. Particular examples of such agents include tacrine, donepezil (e.g., ARICEPT), rivastigmine (e.g., EXELON and EXELON PATCH), galantamine (e.g., RAZADYNE), and memantine (e.g., AKATINOL, AXURA, EBIXA/ABIXA, MEMOX and NAMENDA).

Some embodiments of the invention include administering rilapladib Form 3 or a pharmaceutical composition containing the same in a combination therapy with one or more other forms of rilapladib, for any of the uses of rilapladib Form 3 disclosed herein.

Combination therapy includes co-administration of rilapladib Form 3 and said other pharmaceutical agent, sequential administration of rilapladib Form 3 and the other pharmaceutical agent, administration of a composition containing rilapladib Form 3 and the other pharmaceutical agent, or simultaneous administration of separate compositions containing rilapladib Form 3 and the other pharmaceutical agent.

When combined in the same formulation it will be appreciated that the two (or more) pharmaceutical compounds must be stable and compatible with each other and the other components of the formulation and may be formulated together for administration. When formulated separately they may be provided in any convenient formulation, in such a manner as is known for such compounds in the art.

When Form 3 rilapladib is used in combination with a second therapeutic agent, the dose of each compound may differ from that when the compounds are used alone. Appropriate doses will be readily appreciated by those skilled in the art.

The invention includes the use of rilapladib Form 3 for the preparation of a pharmaceutical composition for treating the aforementioned diseases or disorders in a subject in need thereof, wherein the composition comprises rilapladib Form 3 and a pharmaceutically acceptable carrier (e.g., as a mixture).

The invention further includes the use of rilapladib Form 3 as an active therapeutic substance, in particular in the treatment of one or more of the aforementioned diseases or disorders.

In another aspect, the invention includes the use of rilapladib Form 3 in the manufacture of a medicament for use in the treatment of one or more of the aforementioned diseases or disorders.

The rilapladib Form 3 (including as a pharmaceutical composition thereof) may be administered by ocular, oral, nasal, transdermal, topical with or without occlusion, intravenous (both bolus and infusion), or injection (intraperitoneally, subcutaneously, intramuscularly, intratumorally, or parenterally) routes.

"Pharmaceutically acceptable carrier" means any one or more compounds and/or compositions that are of sufficient purity and quality for use in the formulation of drug substance that, when appropriately administered to a human, do not produce an adverse reaction, and that are used as a vehicle for a drug substance (e.g., rilapladib Form 3).

The invention further includes the process for making the pharmaceutical composition comprising combining (e.g., mixing) rilapladib Form 3 and a pharmaceutically acceptable carrier; and includes those pharmaceutical compositions resulting from such a process, which process includes conventional pharmaceutical techniques. For example, rilapladib Form 3 may be nanomilled prior to formulation. Rilapladib Form 3 may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference. Examples of pharmaceutically acceptable carriers and pharmaceutical compositions suitable for use in the present invention include the carriers and compositions disclosed in the above-mentioned WO02/30904A1, WO2008/141176, WO08/140449, WO2012/080497, WO2012/037782, WO2012/075917, WO2012/076435, US 2008/0279846, US2010/0239565 and US2008/0280829.

The pharmaceutical compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, suppository, or a topical solution, ointment, transdermal patch or other transdermal vehicle; for administration ocularly, orally, intranasally, sublingually, parenterally, topically, rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The dosage form containing the pharmaceutical composition of the invention contains an effective amount of the drug substance (rilapladib Form 3 and optionally, one or more other pharmaceutical active agents, for instance as described herein) necessary to provide a therapeutic and/or prophylactic effect.

In some embodiments, the composition which is administered is in unit dose form such as a tablet or capsule. Each dosage unit for oral administration may contain, e.g., from about 1 to about 500 mg (e.g., about 250 mg)(and for parenteral administration from about 0.1 to about 25 mg) of rilapladib Form 3. The daily dosage regimen for an adult patient may be, for example, an oral dose of between about 1 mg and about 1000 mg, e.g., an oral dose of between about 1 mg and about 500 mg, e.g., about 250 mg, or an intravenous, subcutaneous, or intramuscular dose of between about 0.1 mg and about 100 mg, e.g. of between about 0.1 mg and about 25 mg, of rilapladib Form 3, the compound being administered 1 to 4 times per day. Suitably the compound will be administered for a period of continuous therapy, for example for a week or more. It will be understood that in the foregoing dosages, "about" includes the specifically mentioned dosages.

Dosages will vary depending on factors associated with the particular patient being treated (e.g. age, weight, diet, and time of administration), the severity of the condition being treated, the compound(s) being employed, the mode of administration, and the strength of the preparation.

An oral composition is preferably formulated with a pharmaceutically acceptable carrier as a homogeneous composition, wherein the drug substance (rilapladib Form 3 and any optional other pharmaceutical active agent) is dispersed evenly throughout the mixture, which may be readily subdivided into dosage units containing equal amounts of the drug substance. The pharmaceutically acceptable carrier may include one or more compounds known in the art for oral pharmaceutical dosage forms, including for example starch, sugar (e.g., natural sugars, e.g. glucose and beta-lactose), corn sweeteners, diluents (e.g., water), granulating agents, lubricants, glidants, binding agents, disintegrating agents, gelatin, methyl cellulose, agar, bentonite, excipients (e.g., water, glycols, oils, alcohols, flavoring agents, preservatives, coloring agents, and syrup), conventional tableting ingredients (e.g., corn starch, lactose, sucrose, sorbitol, talc, stearic acid, magnesium stearate, dicalcium phosphate, and any of a variety of gums including natural and synthetic gums (e.g. acacia and tragacanth).

Tablets and capsules represent an advantageous oral dosage unit form. Tablets may be sugarcoated or film-coated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

In some embodiments the oral dosage form is a tablet. Appropriate additives in such a tablet may comprise diluents (also known to the person skilled in the art as fillers) such as microcrystalline cellulose, mannitol, lactose (e.g. anhydrous lactose, lactose monohydrate, and mixtures thereof), calcium carbonate, magnesium carbonate, dicalcium phosphate or mixtures thereof; binders such as hydroxypropylmethylcellulose (also known as hypromellose), hydroxypropylcellulose, polyvinylpyrrolidone, pre-gelatinised starch or gum acacia or mixtures thereof; disintegrants such as microcrystalline cellulose (e.g. as both a diluent and disintegrant), cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as poloxamer, desiccating amorphous silica, colouring agents, flavours etc. In some embodiments, the tablet comprises a diluent, binder, lubricant, and a disintegrant, for instance lactose as diluent, a binder (for instance, hydroxypropylmethylcellulose), magnesium stearate as lubricant, croscarmellose sodium as disintegrant, and microcrystalline cellulose as diluent and/or disintegrant. The tablet may be optionally coated, e.g. with a one or more film, seal or enteric coats.

The diluent may be present in a range of 10-80% by weight of the tablet core. The lubricant may be present in a range of 0.25-2% by weight of the core. The disintegrant may be present in a range of 1-10% by weight of the core. Microcrystalline cellulose, if present, may be present in a range of 10-80% by weight of the core.

In some embodiments, the tablet core comprises microcrystalline cellulose, lactose monohydrate, hypromellose, croscarmellose sodium, and magnesium stearate. In some embodiments, the tablet is coated with a film coat, for instance comprising a suitable polymer, plasticizer and optional pigment, such as the OPADRY series of coatings. In some embodiments the film coat comprises hypromellose, polyethylene glycol (e.g., PEG400) and titanium dioxide, for instance, OPADRY OY-S-28876.

For ocular administration, a pharmaceutical composition is preferably in the form of an ophthalmic composition. The ophthalmic compositions are suitably formulated as eye-drop formulations and filled in appropriate containers to facilitate administration to the eye, for example a dropper fitted with a suitable pipette. Preferably, the compositions are sterile and aqueous based, using purified water. In addition to rilapladib Form 3, an ophthalmic composition may contain one or more of: a) a surfactant; b) a thickening agent; c) an anti-oxidant; d) other excipients such as an alcohol, isotonic agent, buffer, preservative, and/or pH-controlling agent. The pH of the ophthalmic composition is desirably within the range of 4 to 8. Ophthalmic compositions are also suitably formulated as an ointment.

Without further elaboration, it is believed that one skilled in the art can, using the preceding description, utilize the present invention to its fullest extent. The following Examples are, therefore, to be construed as merely illustrative and not a limitation of the scope of the present invention in any way.

Abbreviations are used in the following Examples and throughout this disclosure. Unless otherwise indicated, the following abbreviations are defined as indicated:

| | |
|---|---|
| ATR | Attenuated Total Reflectance |
| CDI | 1,1'-carbonyldiimidazole |
| cGMP | current good clinical manufacturing practice |
| DEGDME | diethylene glycol |
| DiMAC | dimethylacetamide |
| DMA | dimethyl acetamide |
| DMSO | dimethylsulfoxide |
| DSC | Differential Scanning Calorimetry |
| EtOAc | ethyl acetate |
| HPLC | High Performance Liquid Chromatography |
| IPA | isopropyl alcohol |
| IPE | isopropyl ether |
| iPrOAc | isopropyl acetate |
| IR | Infrared |
| MDC | dichloromethane |
| MeCN | acetonitrile |
| MEK | methyl ethyl ketone |
| MeOAc | methyl acetate |
| MeOH | methanol |
| MIBK | methylisobutylketone |
| MS (EI) | Mass Spectrometry (Electron Ionization) |
| NMP | methyl pyrrolidone |
| NMR | Nuclear Magnetic Resonance |
| PEG | polyethylene glycol |
| TBME | t-butyl methyl ether |
| TBTU | (O-(Benzotriazol-1-yl)-N,N,N',N'-tetramethyluronium tetrafluoroborate) |
| TFA | trifluoroacetic acid |
| TG | thermogravimetry |
| THF | tetrahydrofuran |
| XRPD | X-Ray Powder Diffraction |

Other abbreviations used herein have their ordinary meaning.

EXAMPLE 1

Comparative—a Preparation of Form 1 Rilapladib (a) Preparation of Rilapladib to cGMP (Current Good Clinical Manufacturing Practice)

For a preparation of [2-(2,3-difluorobenzylthio)-4-oxo-4H-quinolin-1-yl]acetic acid and N-(1-(2-methoxyethyl)piperidin-4-yl)-4-(4-trifluoromethylphenyl)benzylamine see, e.g. WO02/30904.

[2-(2,3-difluorobenzylthio)-4-oxo-4H-quinolin-1-yl]acetic acid (54.0 g, 0.15 mol), N-(1-(2-methoxyethyl)piperidin-4-yl)-4-(4-trifluoromethylphenyl)benzylamine (58.6 g, 0.15 mol, 1.0 eq) and dichloromethane (MDC) (900 ml) were charged to a 3 L round-bottom flask with stirring under nitrogen. Triethyl amine (56.4 ml, 41.0 g, 0.4 mol, 2.7 eq) and TBTU (O-(Benzotriazol-1-yl)-N,N,N', N'-tetramethyluronium tetrafluoroborate) (52.7 g, 0.16 mol, 1.1 eq) were added and the mixture stirred at room temperature. After approximately 15 minutes a red solution was obtained. After about 2 hours the mixture was quenched by addition of 2M aqueous HCl (500 ml) and left to stir for 10 minutes. 2M aqueous NaOH (600 ml) was added slowly with water bath cooling. The organic layer was separated and washed with water (500 ml) (the separation was slow). The MDC solution was dried over sodium sulphate (100 g), filtered and the residue washed with MDC (100 ml). Evaporation gave a red oil (130 g). This was dissolved in ethyl acetate (500 ml) and filtered into a 2 L round bottom flask. Heptane (500 ml) was added and the mixture left to stir for 1 hour at room temperature. After 1 hour at 0-5° C. the product was filtered and the residue washed with MDC (100 ml). Separation gave a red oil (130 g). This was dissolved in ethyl acetate (500 ml) and filtered into a 2 L round bottom flask. Heptane (500 ml) was added and the mixture left to stir for 1 hour at room temperature. After 1 hour at 0-5° C. the product was filtered and washed with heptane (100 ml). Drying in the vacuum oven at 35° C. overnight gave a pale pink solid (89 g, 81%). HPLC showed 98.46% rilapladib; total impurities 1.54%; largest impurity 0.47% (Column: 50×2.1 mm XTerra MS C18 3.5 um, Column temp:40° C., Eluent A:0.1% v/v TFA (trifluoroacetic acid) in $H_2O$, Eluent B:0.1% v/v TFA in MeCN, Flow rate:0.25 mL min-1, Gradient: 15-40% B in 15 mins; 20 mins@40% B, 40-90% B in 15 mins, 90-15% B in 1 min; 9 min re-equilibration, Sample prep:~0.3 mg in 1.0 mL MeCN+1.0 mL H2O, Inj. vol:10 uL, Detection:UV at 254 nm).

(b) Recrystallization of Rilapladib Prepared in (a) Above, to cGMP

Rilapladib from step (a) (85 g) was dissolved in ethyl acetate (375 ml) with heating and the solution filtered using a Buchner funnel. The solution was charged to a 2 L flask and rinsed in with ethyl acetate (50 ml). Heptane (425 ml) was added and the mixture heated to 70° C. A clear solution was not obtained so further ethyl acetate (75 ml, then 100 ml) was added until a solution was obtained. The solution was cooled to 40° C. and seed (rilapladib prepared under step (a) above, 100 mg) was added. The mixture was allowed to cool to room temperature over approximately 1 hour, then stirred at 0-5° C. for 1 hour. The product was filtered, washed with 1:1 ethyl acetate:heptane (100 ml) and dried overnight in a vacuum oven at 40° C. $^1$H NMR showed some heptane remaining; HPLC showed 99.23% rilapladib; total impurities 0.77%; largest impurity 0.26% (HPLC conditions as for step (a)). After drying for a further night NMR showed virtually no heptane. The product rilapladib (76.2 g, 90%) was analyzed and found to be consistent with Form 1 rilapladib.

(c) Preparation of Rilapladib to cGMP

[2-(2,3-difluorobenzylthio)-4-oxo-4H-quinolin-1-yl]acetic acid (70.0 g, 0.193 mol), N-(1-(2-methoxyethyl)piperidin-4-yl)-4-(4-trifluoromethylphenyl)benzylamine (76.0 g, 0.193 mol) and dichloromethane (MDC) (1.15 L) were charged to a 3 L round-bottom flask with stirring under nitrogen. Triethylamine (72.9 ml, 52.9 g, 0.523 mol, 2.7 eq) and TBTU (68.4 g, 0.213 mol, 1.1 eq) were added and the mixture stirred at ambient temperature for one hour. One drop of the reaction mixture was dissolved in 5 ml of methanol and analyzed by HPLC, which showed 71% rilapladib (Column—symmetry C8, 5 μm, 3.9×150 mm; flow —1 ml/min; Temp—ambient; Wavelength—254 nm; Gradient—90% of 0.1% TFA in water, 10% acetonitrile ramped to 90% acetonitrile over 10 minutes, held for 8 minutes and ramped back to 10% acetonitrile). The mixture was quenched by addition of 2M hydrochloric acid (500 ml) and left to stir for half an hour. 2M aqueous NaOH (600 ml) was added slowly with water bath cooling. The organic layer was separated and washed with water (500 ml). The MDC solution was dried over sodium sulphate (100 g), filtered and the residue washed with MDC (100 ml). Evaporation gave an orange oil (190 g). This was dissolved in ethyl acetate (650 ml) and filtered into a 2 L, 3 necked round bottom flask. Heptane (650 ml) was added followed by rilapladib seed (100 mg, prepared according to step (b) above). After 1 hour at 20-25° C. and 1 hour at 0-5° C. the product was filtered and washed with 1:1 ethyl acetate:heptane (100 ml). Drying overnight in the vacuum oven (18 hours) at 40° C. gave rilapladib as a beige solid (100.0 g, 70%).

(d) Purification and Recrystallization of Rilapladib From (c)

45 g of rilapladib from step (c) was purified by silica gel chromatography in 25 and 20 g lots. Each was columned with 250 g of silica gel using 5% methanol in MDC (3 L each). The product fractions were combined and evaporated to dryness. The yellow foam was dissolved in ethyl acetate (200 ml), filtered into a 1 L 3-necked round-bottom flask and washed in with ethyl acetate (100 ml). The solution was warmed to 50° C. and heptane (200 ml) added. At 40° C. rilapladib seed (100 mg) was added and the slurry stirred for 1 hour at ambient and 2 hours at 0-5° C. The product was filtered, washed with heptane (50 ml) and dried in a vacuum oven at 40° C. This gave rilapladib as an off-white solid (36.7 g, 82%). HPLC showed 98.94% rilapladib; 1.06% impurities; largest impurity 0.21% (HPLC conditions as in step (a)). NMR showed no solvent.

The product was characterized in several ways and determined to be the form termed Form 1 rilapladib. It provided an XRPD pattern as represented in FIG. 3, a Raman spectrum as represented in FIG. 4, and a capillary melting point of 116-118° C. In addition, it exhibited a DSC endotherm of 110° C. and a 0.04% weight loss by TG (thermogravimetry), and was characterized by Dynamic Vapor Sorption as a—non-hygroscopic, crystalline anhydrate.

XRPD instrument/acquisition details were as follows. Powder patterns were obtained using a Bruker D8 Advance X-Ray powder diffractometer configured with a Cu anode (40 kV, 40 mA), variable divergence slit, primary and secondary Soller slits, and a position sensitive detector. Data were acquired over the range 2-35 degrees 2-theta (Copper K-alpha radiation) using a step size of 0.0145 degrees 2-theta (time per step: 1 s). Samples (lightly ground) were packed into top-filled cups that were rotated during data acquisition.

The XRPD pattern is shown in FIG. 3 and is representative of Form 1 rilapladib. The following peaks may be particularly useful for identifying Form 1: 5.5, 5.9, 8.8, 10.9, 11.5, 11.8, 12.3, 14.5, 15.7, 16.6, 17.4, 18.2, 18.5, 20.4, 22.0, 23.3, and 24.2 degrees (±0.1 degrees respectively); peaks 5.5, 8.8, 10.9, 14.5 and 18.2 degrees (±0.1 degrees respectively) may be particularly useful. As will be appreciated by those skilled in the art, these peaks do not represent an exhaustive list of peaks exhibited by Form 1 rilapladib. In addition, while the aforementioned peaks may be useful for identifying Form 1, identification of an unknown sample of rilapladib is preferably carried out by comparison of the full XRPD to that of FIG. 3 as described herein above.

Raman data were acquired on a Nicolet FT-Raman 960 E.S.P., using 1064 nm excitation at 400 mW power. The resolution of the scans was 4 cm$^{-1}$. Specific details are described herein above.

The Raman spectrum is shown in FIG. 4 and is representative of Form 1 rilapladib. Bands which may be useful for identifying Form 1 include band positions at 86, 112, 158, 181, 263, 519, 528, 615, 629, 694, 739, 746, 764, 777, 808, 822, 1036, 1164, 1180, 1290, 1344, 1471, 1526, 1576, 1613, 1619, 2928, 2955, 3064, and 3080 cm$^{-1}$ (±1 cm$^{-1}$ respectively); band positions at 86, 112, 263, 746, 1164, 1344, 1619, 3064, and 3080 cm$^{-1}$ (±1 cm$^{-1}$ respectively) may be particularly indicative. Peak positions of significant peaks rounded to the nearest whole wavenumber include 3064, 2955, 1619, 1576, 1526, 1344, 1290, 1180, 808, 112, and 86 cm$^{-1}$. These bands, ±1 cm$^{-1}$ respectively, may be useful for identifying Form 1. As will be appreciated by those skilled in the art, these bands do not represent an exhaustive list of peaks exhibited by Form 1 rilapladib. In addition, while the aforementioned bands may be useful for identifying Form 1, as described above identification of an unknown sample of rilapladib is preferably carried out by comparison of the full Raman spectrum to that of FIG. 4.

EXAMPLE 2

Comparative—A Preparation of Form 2 Rilapladib

Form 1 rilapladib was recrystallized by slow evaporation from toluene. 500 mg of rilapladib Form 1 prepared in accordance with Example 1(d) was dissolved in toluene (5-10 volumes) with heating. The solution was allowed to evaporate over a weekend. The solids were isolated and properties determined. The resulting rilapladib solids provided Raman and XRPD spectra different from that of Example 1(d), and was designated Form 2 rilapladib. As noted above, Form 2 is less well defined than Form 1 and, while broadly similar and clearly related, "Form 2" solid state characterizations may vary depending on the solvent composition.

This preparation of rilapladib provided a Raman spectrum represented by FIG. 6, an XRPD pattern represented by FIG. 5, and a capillary melt point of 114-116° C. In addition, the product exhibited a DSC endotherm of 109° C. and a weight loss of 1.7% by thermogravimetry. NMR showed 3.4% toluene.

FIG. 5 represents an XRPD spectrum of this sample of Form 2 rilapladib. FIG. 6 represents a Raman spectrum of this sample of Form 2 rilapladib. XRPD and Raman instrument/acquisition details were as in Example 1. Raman peak positions of significant peaks rounded to the nearest whole wavenumber include: 3063, 2947, 1612, 1576, 1528, 1343, 1290, 1180, 1164, 806, 112, and 80 cm$^{-1}$. These bands, ±1 cm$^{-1}$ respectively, may be useful for identifying Form 2. However, identification of an unknown sample of rilapladib is preferably carried out by comparison of the full spectrum to that of FIG. 5 or 6, as applicable, as described herein above.

EXAMPLE 3

Preparation of Rilapladib Form 3 and Other Forms

To mini-reaction vials (2 per each solvent used), approximately 1 mL of solvent was added. The solvents used were acetonitrile, THF(tetrahydrofuran), ethyl acetate, toluene, heptane, acetone, and aqueous ethanol. Rilapladib Form 1 prepared in accordance with Example 1(d) was added and stirred at 10° C. until a slurry formed (in the case of aqueous ethanol, a biphasic mixture formed with a gel-like bottom layer). The mixtures were stirred overnight at 10° C., then the temperature was increased to 30° C., causing dissolution of the crystals that had formed in the solvents other than aqueous ethanol. The mixtures were then cooled to 10° C., which resulted in recrystallization of the solids.

For one set of vials (A) (1 per each solvent used), the solids were isolated after further aging for 3 hours at 10° C. The second set (B) of vials was seeded with crystals from set 1 and held at 10° C. over the weekend (about 3 days).

The solids were isolated and found to exhibit the following melting points (capillary tube) and DSC onset endotherms:

| Solvent | | 1$^{st}$ set (A) | | | 2$^{nd}$ set (B) | |
|---|---|---|---|---|---|---|
| | | Melting point ° C. | DSC ° C. | | Melting point ° C. | DSC ° C. |
| Acetonitrile | A1: | 179.9 | 170 | B1: | 180.9-182.2 | 170 |
| THF | A2: | 112.3-121.8 | 103 | B2: | 2 melts: 113.8-120.6; 175.3-176.6 | 104; 161 |
| ethyl acetate | A3: | 2 melts: 112.1-118.9; 176.5-179.9 | 110; 175 | B3: | 174.5-177.3 | 171 |
| Toluene | A4: | 115.5 | 104 | B4: | 173.9-178.3 | 100; 170 |
| Heptane | A5: | 112.5-122.2 | 105; 160 | B5: | 116.4-126.6 | 108; 162 |
| Acetone | A6: | 178.2-179.5 | 171 | B6: | 173.3-176.6 | 172 |

The X-ray powder diffraction pattern of the material from the 1$^{st}$ set, acetonitrile crystallized product (A1) is shown in FIG. 1 and is representative of Form 3 rilapladib. The following peaks may be particularly useful for identifying Form 3: diffraction angles (2 theta) at positions of 6.2, 7.6, 9.1, 11.2, 11.7, 12.4, 13.1, 14.0, 14.3, 14.9, 15.3, 16.5, 16.8, 17.5, 17.8, 18.5, 18.9, 19.3, 20.0, 20.6, 21.1, and 22.1 degrees (±0.1 degrees respectively); diffraction angles (2 theta) at positions 6.2, 7.6, 9.1, 11.2, and 14.3 degrees (±0.1 degrees respectively) may be particularly useful. Those skilled in the art will appreciate that these peaks do not represent an exhaustive list of peaks exhibited by Form 3 rilapladib. In addition, while the aforementioned peaks may be useful for identifying Form 3, identification of an unknown sample of rilapladib is preferably carried out by comparison of the full XRPD to that of FIG. 1 as described herein above. FIG. 1 does not indicate the presence of Form 1 or Form 2 rilapladib, considering a detectability of about 2% of either form in Form 3.

The Raman spectrum of the material from the 1st set, acetonitrile crystallized product (A1) is shown in FIG. 2 and is representative of Form 3 rilapladib. The following bands may be particularly useful for identifying Form 3: bands at positions of 103, 159, 186, 276, 519, 524, 613, 628, 694, 736, 752, 766, 776, 808, 820, 1038, 1155, 1179, 1288, 1336, 1467, 1528, 1576, 1611, 1623, 2933, 2952, and 3075 cm$^{-1}$ (±1 cm$^{-1}$ respectively) (e.g., bands at positions of 103, 808, 1155, 1179, 1288, 1336, 1467, 1528, 1576, 1611, 1623, 2952, and 3075 cm$^{-1}$ (±1 cm$^{-1}$ respectively)). Bands at positions 103, 276, 752, 1155, 1336, 1623, and 3075 cm$^{-1}$ (±1 cm$^{-1}$ respectively)may be particularly indicative. Those skilled in the art will appreciate that these bands do not represent an exhaustive list of bands exhibited by Form 3 rilapladib. In addition, while the aforementioned bands may be useful for identifying Form 3, as described above identification of an unknown sample of rilapladib is preferably carried out by comparison of the full Raman spectrum to that of FIG. 2.

XRPD and Raman analysis of the other isolated solids is summarized below:
- (A2)—Raman and XRPD spectra were similar to those of Example 2.
- (A3)—the Raman spectrum was like that of Example 1(d) and 2 combined.
- (A4)—Raman and XRPD spectra were similar to that of Example 2.
- (A5)—Raman and XRPD spectra was consistent with that of Example 1(d).
- (A6)—Raman and XRPD spectra were consistent with that of (A1).
- (B1)—Raman and XRPD spectra were consistent with that of (A1).
- (B2)—Raman and XRPD spectra were similar to that of Example 2.
- (B3)—Raman and XRPD spectra were consistent with that of (A1).
- (B4)—The Raman spectrum indicated a mixture of forms. XRPD was like that of (A1) and Example 2 combined.
- (B5)—the Raman spectrum was like that of Example 1(d) and 2 combined. XRPD was consistent with that of Example 1(d).
- (B6)—Raman and XRPD spectra were consistent with that of (A1).

XRPD and Raman instrument/acquisition details for the products of Example 3 were as in Example 1.

The XRPD, Raman and/or melting points of the 1st set acetonitrile and acetone crystallizations (A1 and A6) and the 2nd set acetonitrile, ethyl acetate, toluene and acetone (B1, B3, B4, B6) crystallizations are indicative of the presence of Form 3 rilapladib. Where 2 melting points were observed, a mixture of rilapladib forms, including Form 3, may be present. The lower melt points of about 110-130° C. (e.g., about 112-127° C.) are indicative of the presence of Form 1 or another form (other than Form 3). All samples may include a form of rilapladib other than Form 3.

EXAMPLE 4

A Preparation of Form 3 Rilapladib

Form 1 rilapladib was slurried in the seven solvents used in Example 3 for 2 days at 50° C. Rilapladib Form 1 prepared in accordance with Example 1(d) was added to solvent until a slurry formed and the solids were isolated. Capillary melting points and DSC onset endotherms for the isolated crystalline materials were as follows:

| Solvent | Melting point ° C. | DSC ° C. |
|---|---|---|
| Acetonitrile | 175.1-177.8 | 172 |
| THF | 175.7-177.7 | 172 |
| ethyl acetate | 173.1-175.9 | 172 |
| Toluene | 173.4-176.8 | 170 |
| Heptane | 171.9-174.6 | 172 |
| Acetone | 175.6-178.4 | 173 |
| Aqueous ethanol | 175.9-178.6 | 172 |

XRPD and Raman patterns for the isolated crystalline materials were consistent with those described in Example 3, indicating that rilapladib Form 3 had formed. The melting points of the isolated materials are also indicative of the presence of rilapladib Form 3.

EXAMPLE 5

A Preparation of Form 3 Rilapladib 1 gram of Form 1 rilapladib prepared in accordance with Example 1(d) was dissolved in 5 volumes ethyl acetate at 50° C. The solution started to crystallize. It was cooled to 0° C. and the crystalline material was isolated and dried in a vacuum oven for 1 hour (recovered 0.87 g, capillary melt point 173.8-180.0° C., DSC onset endotherm 171° C.).

XRPD and Raman patterns for the isolated crystalline material were consistent with those described in Example 3, indicating that rilapladib Form 3 had formed. The melting point of the isolated material is also indicative of the presence of rilapladib Form 3.

EXAMPLE 6

A Preparation of Form 3 Rilapladib 1 gram of Form 1 rilapladib prepared in accordance with Example 1(d) was dissolved in 5 mL ethyl acetate at 60° C. 5 mL heptane was added, the mixture was cooled to 50° C. and then seeded with Form 3 rilapladib crystallized from Form 1 slurried in acetonitrile at 50° C. for 2 days. The mixture was cooled to 0° C. and the crystalline material was isolated and dried in a vacuum oven for 1 hour (recovered 0.93 g, capillary melt point 173.8-175.1° C., DSC onset endotherm 170° C.).

XRPD and Raman patterns for the isolated crystalline materials were consistent with those described in Example 3, indicating that rilapladib Form 3 had formed. The melting point of the isolated material is also indicative of the presence of rilapladib Form 3.

EXAMPLE 7

A Preparation of Form 3 Rilapladib 1 gram of Form 1 prepared in accordance with Example 1(d) was dissolved in 10 mL ethyl acetate at 50° C. The mixture was seeded with Form 3 rilapladib crystallized from Form 1 slurried in acetonitrile at 50° C. for 2 days. The mixture was cooled to 0° C. and the crystalline material was isolated and dried in a vacuum oven for 1 hour (recovered 0.85 g, capillary melt point 174.0-176.0° C., DSC onset endotherm 171° C.).

XRPD and Raman patterns for the isolated crystalline material were consistent with those described in Example 3, indicating that rilapladib Form 3 had formed. The melting point of the isolated material is also indicative of the presence of rilapladib Form 3.

EXAMPLE 8

A Preparation of Form 3 Rilapladib

Rilapladib Form 1 prepared in accordance with Example 1(d) (1 gram) was charged to a 10 mL round-bottomed flask with ethyl acetate (5 mL). The mixture was heated to 50° C. to give a solution, then left to stir at 50° C. After several hours, the mixture was cooled to 0-5° C. and stirred for one hour. The product was filtered, washed and dried in the vacuum oven to give a white solid (960 mg, 94%; capillary melting point 169-170° C.; DSC onset endotherm 172° C.). XRPD and Raman patterns for the isolated material were consistent with those described in Example 3, indicating that rilapladib Form 3 had formed. The melting point of the isolated product is also indicative of the presence of rilapladib Form 3.

EXAMPLE 9

A Preparation of Form 3 Rilapladib

Rilapladib is prepared from an amide coupling reaction between the corresponding amine and acid (see, e.g. WO02/30904) in accord with the following: a) The acid is heated initially with 1,1'-carbonyldiimidazole ("CDI") in a mixture of MIBK and DiMAC. The amine is added and the rilapladib so formed is isolated by washing the reaction mixture with water and aqueous sodium bicarbonate, concentrating the MIBK solution and crystallization (a rilapladib Form 3 seed is optionally used); b) the rilapladib is recrystallized from MIBK (a rilapladib Form 3 seed may be used).

a) Preparation of Rilapladib

[2-(2,3-difluorobenzylthio)-4-oxo-4H-quinolin-1-yl]acetic acid (15.0 g) as a solution in a mixture of dimethylacetamide (DiMAC, 15 mL) and methylisobutylketone (MIBK, 95 mL) at 60° C. is treated with 1,1'-carbonyldiimidazole CDI (7.41 g) portionwise over ca. 30 minutes and then stirred for a further 30 minutes to form the imidazolide.

N-(1-(2-methoxyethyl)piperidin-4-yl)-4-(4-trifluoromethylphenyl)benzylamine (16.29 g), dissolved in MIBK (30 mL), is added to the above imidazolide and the mixture heated and stirred at 83° C. until the reaction is complete (2-4 h). The DiMAC/MIBK solution containing the crude reaction product (N-[1-(2-methoxyethyl)-piperidin-4-yl]-2-[2-(2,3-difluorobenzylthio)-4-oxo-4H-quinolin-1-yl]-N-(4'-trifluoromethylbiphenyl-4-ylmethyl)acetamide) is then cooled (45° C.), diluted with MIBK (45 mL), washed with water (1×60 mL), 5% w/v aqueous $Na_2CO_3$ (2×60 mL) and finally water (1×60 mL). The MIBK solution is then concentrated to ca. 120 mL (88-118° C., at atmospheric pressure). The solution is cooled to 45° C., seeded with rilapladib Form 3 (15 mg) and stirred for at least 12 hours at 45° C. The resulting slurry is cooled to 20° C. over at least an hour, stirred for at least a further 3 hours and filtered off. The filter cake is washed with MIBK (1×30 mL) and dried in vacuo at 50° C. to yield crystalline rilapladib, Form 3: 25.90 g, 85%. HPLC 99.85% purity (the HPLC method used the following equipment/conditions:Detection: UV; Column: Phenomenex Luna C18 50×2.1 mm id 5 micron; Temperature: 40-60° C.; Flow Rate: 1-2 ml/min; Mobile Phase: A=Water 0.05% TFA; B=Acetonitrile 0.05% TFA; Gradient elution 0% B to 95% B over 8 minutes; Equilibration Time: 0.5-2 min (within gradient programme); Injection Volume: 1 µL; Sample Prep: 2-3 drops in 5 ml of 1:1 acetonitrile:water).

Hplc retention time: 5.0 min (detection at λ=254 nm).

$^1$H nmr (400 MHz, D4-MeOH): 5 8.2-8.35 (1H, m), 7.35-7.85 (11H, m), 6.95-7.3 (3H, m), 6.44+6.52 (1H, 2×s), 5.31+5.68 (2H, 2×s), 4.71+4.87 (2H, 2×br s), 4.37+4.48 (2H, 2×s), 4.4-4.5+3.9-4.05 (1H, 2×m), 3.45-3.55 (2H, m), 3.3 (3H, s), 2.95-3.1 (2H, m), 2.5-2.65 (2H, m), 2.05-2.3 (2H, 2×t), 1.7-2.05 (4H, m).

MS (El): found (M+1): 736; $C_{40}H_{38}F_5N_3O_3S$ requires 735.

b) Recrystallization of Rilapladib

Rilapladib Form 3 (30.0 g, 40.77 mmol, 1 wt) and MIBK (210 mL, 7 vol) are heated at 90° C. to obtain a solution. The solution is filtered and the filter washed with further hot (70-90° C.) MIBK (30 mL, 1 vol). The combined filtrates are cooled to 45° C., seeded with rilapladib Form 3 (30 mg, 0.1% wt) and stirred at 45° C. for at least 15 h. The resultant slurry is cooled to 20° C. over at least one hour and stirred at 20° C. for at least 3 hours. The product is isolated by filtration, washed with MIBK (1×36 mL, 1×1.2 vol) and dried in vacuo at 50° C. to yield rilapladib Form 3 as a white crystalline solid: 26.55 g, 88.5%. HPLC 99.9% (conditions as in part a) of this Example 9). The product characterization data/methodology is the same as described in part a) of this Example 9.

EXAMPLE 10

ATR-IR Form 3 and Form 1 (Comparative)

FIG. 7 is an ATR-IR spectrum of another preparation of rilapladib Form 3. Peak positions of significant peaks rounded to the nearest whole wavenumber include: 2931, 1652, 1621, 1595, 1528, 1494, 1478 1423, 1403, 1327, 1317, 1286, 1237, 1204, 1187, 1166, 1140, 1109, 1066, 1024, 992, 969, 932, 865, 859, 813, 795, 767, 751, 708, and 693 (+/−1 wavenumber for each of the foregoing particular wavenumbers).

FIG. 8 is an ATR-IR spectrum of another preparation of rilapladib Form 1. Peak positions of significant peaks rounded to the nearest whole wavenumber include: 2928, 1652, 1620, 1598, 1527, 1495, 1478, 1468, 1401, 1329, 1297, 1271, 1240, 1201, 1187, 1164, 1143, 1112, 1071, 1030, 1016, 1005, 994, 973, 933, 845, 822, 789, 755, 746, 712, 693, and 665 (+/−1 wavenumber for each of the foregoing particular wavenumbers).

The equipment and acquisition details were as described herein above in reference to FIGS. 7 and 8. Those skilled in the art will appreciate that slight variations in observed peaks are expected based upon the specific spectrometer employed and acquisition parameters used. However, this variation should be no more than ±1 wavenumber.

What is claimed:

1. Crystalline rilapladib characterized by an X-ray powder diffraction pattern substantially in accordance with FIG. 1; and wherein the crystalline rilapladib is substantially pure.

2. Crystalline rilapladib characterized by an X-ray powder diffraction pattern comprising diffraction angles (2 theta) at least at positions of about 6.2, 7.6, 9.1, 11.2, and 14.3 degrees; and wherein the crystalline rilapladib is substantially pure.

3. Crystalline rilapladib according to claim 1, further characterized by a Raman spectrum substantially in accordance with FIG. 2.

4. Crystalline rilapladib according to claim 1, further characterized by a melting point of from about 165° C. to about 185° C.

5. Crystalline rilapladib according to claim 1, further characterized by an ATR-IR absorption spectrum substantially in accordance with FIG. 7.

6. Crystalline rilapladib according to claim 2, further characterized by a Raman spectrum comprising peaks at least at positions of about 103, 276, 752, 1155, 1336, 1623, and 3075 cm$^{-1}$.

7. Crystalline rilapladib according to claim 2, further characterized by an ATR-IR absorption spectrum comprising peaks at least at about wavenumbers 2931, 1652, 1621, 1595, 1528, 1494, 1478 1423, 1403, 1327, 1317, 1286, 1237, 1204, 1187, 1166, 1140, 1109, 1066, 1024, 992, 969, 932, 865, 859, 813, 795, 767, 751, 708, and 693.

8. Crystalline rilapladib according to claim 1, wherein the crystalline rilapladib is at least 95% pure by weight.

9. Crystalline rilapladib according to claim 1, wherein the crystalline rilapladib is at least 97% pure by weight.

10. Crystalline rilapladib according to claim 1, wherein the crystalline rilapladib is at least 99% pure by weight.

11. Crystalline rilapladib according to claim 2, wherein the crystalline rilapladib is at least 95% pure by weight.

12. Crystalline rilapladib according to claim 2, wherein the crystalline rilapladib is at least 97% pure by weight.

13. Crystalline rilapladib according to claim 2, wherein the crystalline rilapladib is at least 99% pure by weight.

14. A pharmaceutical composition comprising crystalline rilapladib according to claim 1 and a pharmaceutically acceptable carrier.

15. A pharmaceutical composition comprising crystalline rilapladib according to claim 2 and a pharmaceutically acceptable carrier.

16. A pharmaceutical composition comprising crystalline rilapladib according to claim 3 and a pharmaceutically acceptable carrier.

17. A pharmaceutical composition comprising crystalline rilapladib according to claim 6 and a pharmaceutically acceptable carrier.

18. A pharmaceutical composition comprising crystalline rilapladib according to claim 8 and a pharmaceutically acceptable carrier.

19. A pharmaceutical composition comprising crystalline rilapladib according to claim 11 and a pharmaceutically acceptable carrier.

20. A pharmaceutical composition comprising crystalline rilapladib according to claim 9 and a pharmaceutically acceptable carrier.

21. A pharmaceutical composition comprising crystalline rilapladib according to claim 12 and a pharmaceutically acceptable carrier.

22. A pharmaceutical composition comprising crystalline rilapladib according to claim 10 and a pharmaceutically acceptable carrier.

23. A pharmaceutical composition comprising crystalline rilapladib according to claim 13 and a pharmaceutically acceptable carrier.

24. Crystalline rilapladib according to claim 2 wherein the X-ray powder diffraction pattern comprises diffraction angles (2 theta) at least at positions of about 6.2, 7.6, 9.1, 11.2, 11.7, 12.4, 13.1, 14.0, 14.3, 14.9, 15.3, 16.5, 16.8, 17.5, 17.8, 18.5, 18.9, 19.3, 20.0, 20.6, 21.1, and 22.1 degrees.

25. Crystalline rilapladib according to claim 2, further characterized by a Raman spectrum comprising peaks at least at positions of about 103, 159, 186, 276, 519, 524, 613, 628, 694, 736, 752, 766, 776, 808, 820, 1038, 1155, 1179, 1288, 1336, 1467, 1528, 1576, 1611, 1623, 2933, 2952, and 3075 cm$^{-1}$.

26. Crystalline rilapladib according to claim 24, further characterized by a Raman spectrum comprising peaks at least at positions of about 103, 159, 186, 276, 519, 524, 613, 628, 694, 736, 752, 766, 776, 808, 820, 1038, 1155, 1179, 1288, 1336, 1467, 1528, 1576, 1611, 1623, 2933, 2952, and 3075 cm$^{-1}$.

27. Crystalline rilapladib according to claim 2, further characterized by a melting point of from about 165° C. to about 185° C.

28. A pharmaceutical composition comprising crystalline rilapladib according to claim 24 and a pharmaceutically acceptable carrier.

29. A pharmaceutical composition comprising crystalline rilapladib according to claim 25 and a pharmaceutically acceptable carrier.

30. A pharmaceutical composition comprising crystalline rilapladib according to claim 26 and a pharmaceutically acceptable carrier.

* * * * *